United States Patent
van Dort et al.

(10) Patent No.: US 12,246,171 B2
(45) Date of Patent: Mar. 11, 2025

(54) CARDIAC ASSIST DEVICE WITH HIGH FREQUENCY OPERATION

(71) Applicant: CardiacBooster B.V., Nijmegen (NL)

(72) Inventors: Daniël Immanuel Michaël van Dort, Nijmegen (NL); René Cornelis Henricus van der Burgt, Nijmegen (NL); Florian Niklas Ludwig, Hilversum (NL)

(73) Assignee: CardiacBooster B.V., Nijmegen (NL)

( * ) Notice: Subject to any disclaimer, the term of this patent is extended or adjusted under 35 U.S.C. 154(b) by 0 days.

(21) Appl. No.: 18/500,906

(22) Filed: Nov. 2, 2023

(65) Prior Publication Data
US 2024/0075276 A1    Mar. 7, 2024

Related U.S. Application Data

(63) Continuation of application No. PCT/NL2022/050193, filed on Apr. 7, 2022.

(30) Foreign Application Priority Data

May 3, 2021   (NL) ...................................... 2028130

(51) Int. Cl.
*A61M 60/139*   (2021.01)
*A61M 60/295*   (2021.01)
(Continued)

(52) U.S. Cl.
CPC ........ *A61M 60/139* (2021.01); *A61M 60/295* (2021.01); *A61M 60/427* (2021.01); *A61M 60/577* (2021.01)

(58) Field of Classification Search
CPC .............. A61M 60/139; A61M 60/427; A61M 60/295; A61M 60/577
(Continued)

(56) References Cited

U.S. PATENT DOCUMENTS

| 3,939,820 A | 2/1976 | Grayzel |
| 4,154,227 A | 5/1979 | Krause et al. |

(Continued)

FOREIGN PATENT DOCUMENTS

| AU | 2018352587 A1 | 4/2020 |
| CN | 1488409 A | 4/2004 |

(Continued)

OTHER PUBLICATIONS

International Search Report and Written Opinion mailed Mar. 18, 2024; International Application No. PCT/EP2023/080613; 23 pages.
(Continued)

*Primary Examiner* — Ankit D Tejani
(74) *Attorney, Agent, or Firm* — FORTEM IP LLP

(57) ABSTRACT

A cardiac assist device with an expandable cup (4) having a transport state and an operational state, the expandable cup comprising a plurality of inflow apertures (5), and an outflow nozzle (6), and an inflatable balloon (8) positioned inside the expandable cup (4). A catheter assembly (3) is connected to the inflatable balloon (8) during operation, and a control unit (2) is connected to the catheter assembly (3). The control unit (2) is arranged to operate the inflatable balloon (8) with a frequency of more than 100 beats per minute.

27 Claims, 10 Drawing Sheets

(51) Int. Cl.
*A61M 60/427* (2021.01)
*A61M 60/577* (2021.01)

(58) Field of Classification Search
USPC .......................................................... 600/18
See application file for complete search history.

(56) References Cited

U.S. PATENT DOCUMENTS

| | | | |
|---|---|---|---|
| 4,785,795 A | 11/1988 | Singh | |
| 4,861,330 A | 8/1989 | Voss | |
| 4,902,272 A | 2/1990 | Milder et al. | |
| 4,906,229 A | 3/1990 | Wampler | |
| 4,946,440 A | 8/1990 | Hall | |
| 5,139,517 A | 8/1992 | Corral | |
| 5,169,378 A | 12/1992 | Figuera | |
| 5,192,314 A | 3/1993 | Daskalakis | |
| 5,484,385 A | 1/1996 | Rishton | |
| 5,749,855 A | 5/1998 | Reitan | |
| 5,820,542 A | 10/1998 | Dobak et al. | |
| 5,827,171 A | 10/1998 | Dobak et al. | |
| 5,928,132 A | 7/1999 | Leschinsky | |
| 6,106,497 A | 8/2000 | Wang | |
| 6,200,260 B1 | 3/2001 | Bolling | |
| 6,210,318 B1 | 4/2001 | Lederman | |
| 6,299,575 B1 | 10/2001 | Bolling | |
| 6,387,037 B1 | 5/2002 | Bolling et al. | |
| 6,390,969 B1 | 5/2002 | Bolling et al. | |
| 6,406,422 B1 | 6/2002 | Landesberg | |
| 6,428,464 B1 | 8/2002 | Bolling | |
| 6,508,777 B1 | 1/2003 | Macoviak et al. | |
| 6,508,787 B2 | 1/2003 | Erbel et al. | |
| 6,610,004 B2 | 8/2003 | Mole et al. | |
| 6,669,624 B2 | 12/2003 | Frazier | |
| 6,685,621 B2 | 2/2004 | Bolling et al. | |
| 6,808,483 B1 | 10/2004 | Ortiz et al. | |
| 6,889,082 B2 | 5/2005 | Bolling et al. | |
| 6,959,711 B2 | 11/2005 | Murphy et al. | |
| 6,994,093 B2 | 2/2006 | Murphy et al. | |
| 7,125,376 B2 | 10/2006 | Mole et al. | |
| 7,144,365 B2 | 12/2006 | Bolling et al. | |
| 7,144,407 B1 | 12/2006 | Lasersohn | |
| 7,331,921 B2 | 2/2008 | Mole et al. | |
| 7,374,531 B1 | 5/2008 | Kantrowitz | |
| 7,458,929 B2 | 12/2008 | Bolling et al. | |
| 7,468,050 B1 | 12/2008 | Kantrowitz | |
| 7,513,863 B2 | 4/2009 | Bolling et al. | |
| 7,588,531 B2 | 9/2009 | Bolling | |
| 7,591,778 B2 | 9/2009 | Bolling | |
| 7,614,997 B2 | 11/2009 | Bolling | |
| 7,655,005 B2 | 2/2010 | Bhola | |
| 7,691,047 B2 | 4/2010 | Ferrari | |
| 7,879,003 B2 * | 2/2011 | Bertolero | A61M 25/003 |
| | | | 604/102.03 |
| 7,914,436 B1 | 3/2011 | Kung | |
| 7,955,248 B2 | 6/2011 | Miller | |
| 7,976,452 B2 | 7/2011 | Kantrowitz | |
| 7,993,260 B2 | 8/2011 | Bolling | |
| 8,016,739 B2 | 9/2011 | Peters et al. | |
| 8,121,684 B2 | 2/2012 | Ross et al. | |
| 8,206,278 B2 | 6/2012 | De et al. | |
| 8,216,122 B2 | 7/2012 | Kung | |
| 8,409,128 B2 | 4/2013 | Ferrari | |
| 8,449,443 B2 | 5/2013 | Rodefeld et al. | |
| 8,469,873 B2 | 6/2013 | Miller et al. | |
| 8,480,555 B2 | 7/2013 | Kung | |
| 8,545,382 B2 | 10/2013 | Suzuki et al. | |
| 8,571,658 B2 | 10/2013 | Peters et al. | |
| 8,579,858 B2 | 11/2013 | Reitan et al. | |
| 8,591,394 B2 | 11/2013 | Peters et al. | |
| 8,628,571 B1 | 1/2014 | Hacohen et al. | |
| 8,702,583 B2 | 4/2014 | Miller | |
| 8,727,959 B2 | 5/2014 | Reitan et al. | |
| 8,900,115 B2 | 12/2014 | Bolling et al. | |
| 8,932,246 B2 | 1/2015 | Ferrari | |
| 9,119,908 B2 | 9/2015 | Peters et al. | |
| 9,308,302 B2 | 4/2016 | Zeng | |
| 9,327,067 B2 | 5/2016 | Zeng et al. | |
| 9,358,329 B2 | 6/2016 | Fitzgerald et al. | |
| 9,358,330 B2 | 6/2016 | Schumacher | |
| 9,364,592 B2 | 6/2016 | McBride et al. | |
| 9,364,593 B2 | 6/2016 | McBride et al. | |
| 9,433,715 B2 | 9/2016 | Kantrowitz et al. | |
| 9,446,179 B2 | 9/2016 | Keenan et al. | |
| 9,545,468 B2 | 1/2017 | Aboul-Hosn et al. | |
| 9,555,176 B2 | 1/2017 | Peters et al. | |
| 9,561,314 B2 | 2/2017 | Aboul-Hosn et al. | |
| 9,561,375 B2 | 2/2017 | Peters et al. | |
| 9,597,437 B2 | 3/2017 | Aboul-Hosn et al. | |
| 9,611,743 B2 | 4/2017 | Toellner et al. | |
| 9,623,163 B1 | 4/2017 | Fischi | |
| 9,675,738 B2 | 6/2017 | Tanner et al. | |
| 9,675,739 B2 | 6/2017 | Tanner et al. | |
| 9,675,740 B2 | 6/2017 | Zeng et al. | |
| 9,717,833 B2 | 8/2017 | McBride et al. | |
| 9,744,281 B2 | 8/2017 | Siegenthaler | |
| 9,770,543 B2 | 9/2017 | Tanner et al. | |
| 9,771,801 B2 | 9/2017 | Schumacher et al. | |
| 9,789,238 B2 | 10/2017 | Aboul-Hosn et al. | |
| 9,827,356 B2 | 11/2017 | Muller et al. | |
| 9,833,550 B2 | 12/2017 | Siess | |
| 9,872,947 B2 | 1/2018 | Keenan et al. | |
| 9,872,948 B2 | 1/2018 | Siess | |
| 9,878,079 B2 | 1/2018 | Pfeffer et al. | |
| 9,889,242 B2 | 2/2018 | Pfeffer et al. | |
| 9,907,890 B2 | 3/2018 | Muller | |
| 9,919,087 B2 | 3/2018 | Pfeffer et al. | |
| 9,962,475 B2 | 5/2018 | Campbell et al. | |
| 9,987,404 B2 | 6/2018 | Tanner et al. | |
| 10,029,037 B2 | 7/2018 | Muller et al. | |
| 10,039,872 B2 | 8/2018 | Zeng et al. | |
| 10,039,873 B2 | 8/2018 | Siegenthaler | |
| 10,071,192 B2 | 9/2018 | Zeng | |
| 10,080,871 B2 | 9/2018 | Schumacher et al. | |
| 10,086,121 B2 | 10/2018 | Fitzgerald et al. | |
| 10,098,992 B2 | 10/2018 | Van Dort et al. | |
| 10,105,475 B2 | 10/2018 | Muller | |
| 10,107,299 B2 | 10/2018 | Scheckel | |
| 10,117,980 B2 | 11/2018 | Keenan et al. | |
| 10,117,982 B2 | 11/2018 | Curtis | |
| 10,137,231 B2 | 11/2018 | Anagnostopoulos | |
| 10,149,932 B2 | 12/2018 | Mcbride et al. | |
| 10,238,783 B2 | 3/2019 | Aboul-Hosn et al. | |
| 10,279,095 B2 | 5/2019 | Aboul-Hosn et al. | |
| 10,300,185 B2 | 5/2019 | Aboul-Hosn et al. | |
| 10,300,186 B2 | 5/2019 | Aboul-Hosn et al. | |
| 10,322,218 B2 | 6/2019 | Aboul-Hosn et al. | |
| 10,328,191 B2 | 6/2019 | Aboul-Hosn et al. | |
| 10,357,598 B2 | 7/2019 | Aboul-Hosn et al. | |
| 10,449,276 B2 | 10/2019 | Pfeffer et al. | |
| 10,449,279 B2 | 10/2019 | Muller | |
| 10,456,514 B2 | 10/2019 | Adlam et al. | |
| 10,478,539 B2 | 11/2019 | Pfeffer et al. | |
| 10,512,714 B2 | 12/2019 | Pfeifer et al. | |
| 10,525,178 B2 | 1/2020 | Zeng | |
| 10,525,238 B2 | 1/2020 | Schumacher et al. | |
| 10,561,773 B2 | 2/2020 | Ferrari et al. | |
| 10,576,192 B2 | 3/2020 | Muller et al. | |
| 10,576,193 B2 | 3/2020 | Tanner et al. | |
| 10,583,232 B2 | 3/2020 | Muller | |
| 10,584,589 B2 | 3/2020 | Schumacher et al. | |
| 10,709,828 B2 | 7/2020 | Toellner et al. | |
| 10,709,829 B2 | 7/2020 | Muller | |
| 10,709,830 B2 | 7/2020 | Tanner et al. | |
| 10,737,005 B2 | 8/2020 | Tanner et al. | |
| 10,765,789 B2 | 9/2020 | Zeng et al. | |
| 10,786,610 B2 | 9/2020 | Zeng | |
| 10,799,624 B2 | 10/2020 | Pfeffer et al. | |
| 10,864,308 B2 | 12/2020 | Muller et al. | |
| 10,864,309 B2 | 12/2020 | McBride et al. | |
| 10,874,781 B2 | 12/2020 | Toellner | |
| 10,874,783 B2 | 12/2020 | Pfeffer et al. | |
| 10,881,770 B2 | 1/2021 | Tuval et al. | |
| 10,881,836 B2 | 1/2021 | Schumacher et al. | |
| 10,894,115 B2 | 1/2021 | Pfeffer et al. | |

(56) References Cited

U.S. PATENT DOCUMENTS

| | | |
|---|---|---|
| 10,898,625 B2 | 1/2021 | Toellner |
| 10,898,626 B2 | 1/2021 | Siegenthaler |
| 10,920,596 B2 | 2/2021 | Toellner et al. |
| 10,960,116 B2 | 3/2021 | Campbell et al. |
| 10,980,927 B2 | 4/2021 | Pfeffer et al. |
| 10,994,120 B2 | 5/2021 | Tuval et al. |
| 11,045,638 B2 | 6/2021 | Keenan et al. |
| 11,058,865 B2 | 7/2021 | Fitzgerald et al. |
| 11,077,294 B2 | 8/2021 | Keenan et al. |
| 11,123,539 B2 | 9/2021 | Pfeffer et al. |
| 11,129,978 B2 | 9/2021 | Pfeffer et al. |
| 11,135,405 B2 | 10/2021 | Schumacher et al. |
| 11,160,970 B2 | 11/2021 | Muller et al. |
| 11,167,124 B2 | 11/2021 | Pfeffer et al. |
| 11,173,297 B2 | 11/2021 | Muller |
| 11,285,309 B2 | 3/2022 | Tuval et al. |
| 11,318,017 B2 | 5/2022 | Besselink |
| 11,351,355 B2 | 6/2022 | Walters et al. |
| 11,400,274 B2 | 8/2022 | Van Dort |
| 11,534,304 B2 | 12/2022 | Thornton et al. |
| 11,583,670 B2 | 2/2023 | Pfeifer et al. |
| 11,602,628 B2 | 3/2023 | Anagnostopoulos |
| 2002/0133227 A1 | 9/2002 | Murphy et al. |
| 2002/0173693 A1* | 11/2002 | Landesberg ........ A61M 60/441 600/16 |
| 2003/0050659 A1 | 3/2003 | Murphy et al. |
| 2003/0074051 A1 | 4/2003 | Freislinger |
| 2004/0097783 A1 | 5/2004 | Peters et al. |
| 2005/0171527 A1 | 8/2005 | Bhola |
| 2005/0228211 A1 | 10/2005 | Leasure |
| 2009/0259089 A1 | 10/2009 | Gelbart et al. |
| 2011/0106120 A1 | 5/2011 | Haselby et al. |
| 2011/0218382 A1 | 9/2011 | Orejola |
| 2011/0270331 A1* | 11/2011 | Peters ............... A61N 1/3627 607/3 |
| 2013/0184515 A1* | 7/2013 | Ovil ............... A61M 60/497 600/17 |
| 2014/0039536 A1 | 2/2014 | Cully et al. |
| 2016/0015877 A1 | 1/2016 | Guerrero et al. |
| 2016/0089482 A1 | 3/2016 | Siegenthaler |
| 2016/0143739 A1 | 5/2016 | Horgan et al. |
| 2017/0056574 A1 | 3/2017 | Pfeifer et al. |
| 2017/0136162 A1 | 5/2017 | Van Dort et al. |
| 2017/0173237 A1 | 6/2017 | Pfeifer et al. |
| 2018/0055981 A1 | 3/2018 | Smith et al. |
| 2018/0303990 A1 | 10/2018 | Siess et al. |
| 2018/0338833 A1 | 11/2018 | Wilson et al. |
| 2019/0083689 A1 | 3/2019 | Anagnostopoulos |
| 2019/0117865 A1* | 4/2019 | Walters ............. A61M 60/40 |
| 2020/0121838 A1 | 4/2020 | Pfeifer et al. |
| 2020/0246527 A1 | 8/2020 | Hildebrand et al. |
| 2020/0268953 A1* | 8/2020 | Ferrari ............ A61B 5/318 |
| 2020/0376179 A1* | 12/2020 | Patzer ............ A61M 60/13 |
| 2021/0113826 A1 | 4/2021 | Smith et al. |
| 2021/0138129 A1 | 5/2021 | Yang et al. |
| 2021/0187274 A1 | 6/2021 | Malkin et al. |
| 2021/0244935 A1 | 8/2021 | Van Dort |
| 2021/0379354 A1 | 12/2021 | Tansley et al. |
| 2022/0032033 A1 | 2/2022 | Besselink et al. |
| 2022/0134081 A1 | 5/2022 | Van Dort et al. |
| 2022/0161017 A1 | 5/2022 | Van Dort |
| 2022/0347460 A1 | 11/2022 | Van Dort |
| 2023/0248961 A1 | 8/2023 | Van Dort et al. |

FOREIGN PATENT DOCUMENTS

| | | |
|---|---|---|
| CN | 1946449 A | 4/2007 |
| CN | 101124002 A | 2/2008 |
| CN | 101448535 A | 6/2009 |
| CN | 101472627 A | 7/2009 |
| CN | 106573090 A | 4/2017 |
| DE | 202007019486 U1 | 12/2012 |
| DE | 102017103350 A1 | 8/2017 |
| EP | 1017430 A1 | 7/2000 |
| EP | 1748808 B1 | 1/2013 |
| EP | 2752209 A1 | 7/2014 |
| EP | 1878453 B1 | 12/2014 |
| EP | 3442614 A0 | 2/2019 |
| EP | 3466458 A1 | 4/2019 |
| EP | 3503939 A0 | 7/2019 |
| EP | 3010563 B1 | 12/2019 |
| EP | 3473279 B1 | 7/2020 |
| EP | 3697464 A2 | 8/2020 |
| EP | 3188769 B1 | 1/2021 |
| EP | 3818997 A1 | 5/2021 |
| EP | 3829670 A0 | 6/2021 |
| EP | 3873555 A0 | 9/2021 |
| WO | 9818508 A1 | 5/1998 |
| WO | 0029057 A1 | 5/2000 |
| WO | 2005102414 A1 | 11/2005 |
| WO | 2011017440 A2 | 2/2011 |
| WO | 2011035925 A1 | 3/2011 |
| WO | 2011117566 A1 | 9/2011 |
| WO | 2014/203078 A2 | 12/2014 |
| WO | 2015131879 A1 | 9/2015 |
| WO | 2015/184450 A1 | 12/2015 |
| WO | 2016001218 A1 | 1/2016 |
| WO | 2016176431 A1 | 11/2016 |
| WO | 2017205909 A1 | 12/2017 |
| WO | 2018075875 A1 | 4/2018 |
| WO | 2018/158635 A1 | 9/2018 |
| WO | 2019/071148 A1 | 4/2019 |
| WO | 2019158420 A9 | 12/2019 |
| WO | WO-2020022905 A1 * | 1/2020 ........ A61M 60/148 |
| WO | 2020/053663 A1 | 3/2020 |
| WO | 2020180176 A1 | 9/2020 |
| WO | 2020180177 A1 | 9/2020 |
| WO | 2021149090 A3 | 10/2021 |
| WO | 2022081009 A1 | 4/2022 |
| WO | 2022126123 A1 | 6/2022 |
| WO | 2022235152 A1 | 11/2022 |
| WO | 2024094821 A1 | 5/2024 |

OTHER PUBLICATIONS

International Search Report and Written Opinion dated Aug. 25, 2022, International Application No. PCT/NL2022/050193, 20 pages.

Rebholz, Mathias, "High-frequency actuation of pulsatile ventricular assist devices", Doctoral Thesis, published on Dec. 2019, 157 pages.

Niu, Yanwen, "Structural Parameters Optimization and Finite Element Analysis of Artificial Heart Pump Impeller", Dissertation for the Master Degree in Engineering, Shenzhen Graduate School, Dec. 2016, 67 pages.

Rüschen, D., et al., "Robust Assistance Control of Left Ventricular Assist Devices", IFMBE Proceedings, vol. 65, Springer Nature Singapore Pte Ltd, 2018, 2 pages.

Yamane, Takashi, et al., "Hemocompatibility of a hydrodynamic levitation centrifugal blood pump", Journal of Artificial Organs, vol. 10, 2007, pp. 71-76.

* cited by examiner

Fig. 1A
Fig. 1B
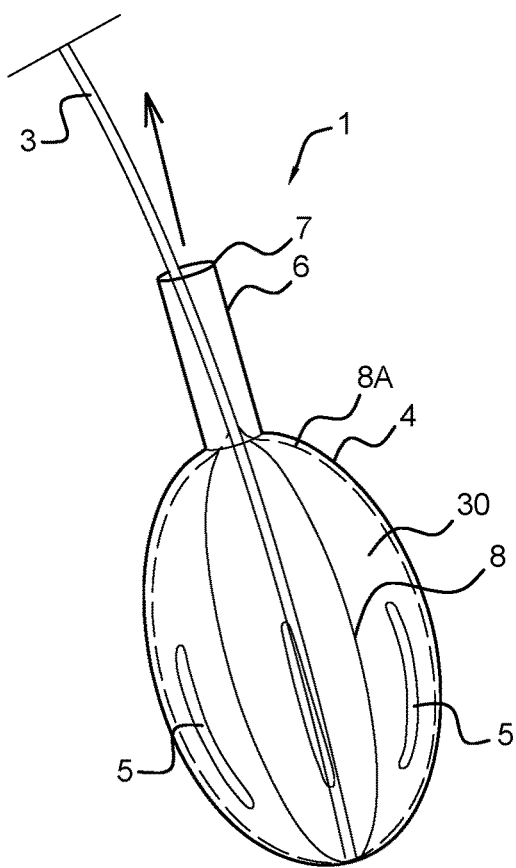
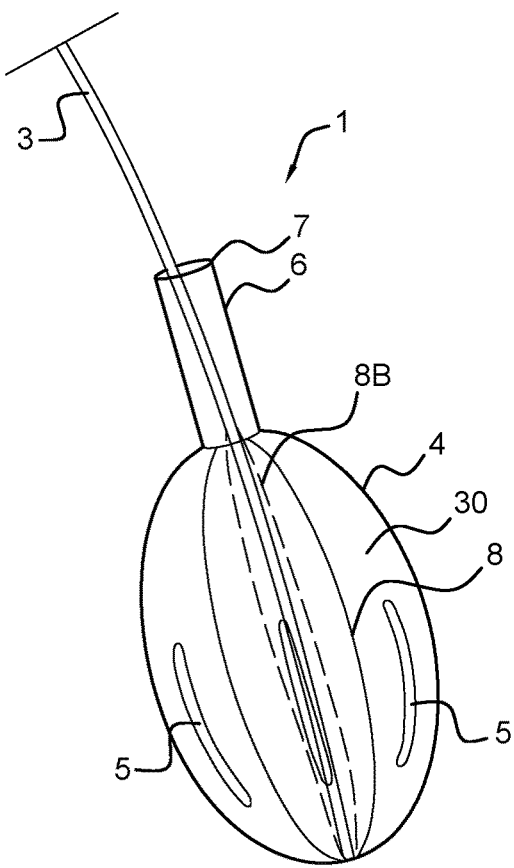
Fig. 2
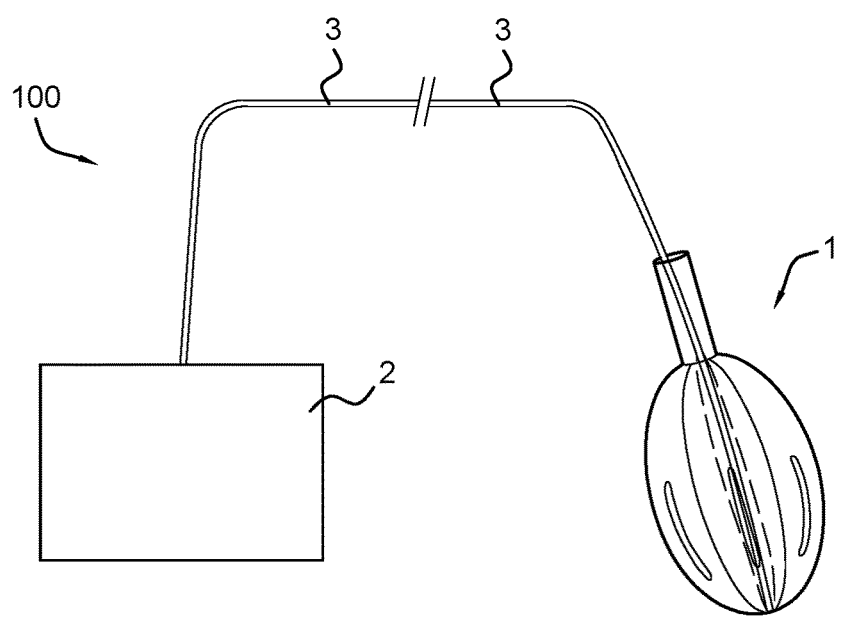

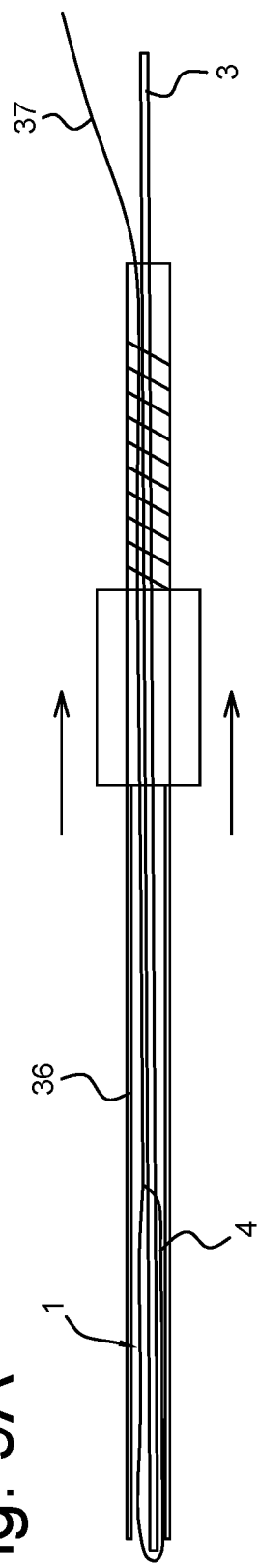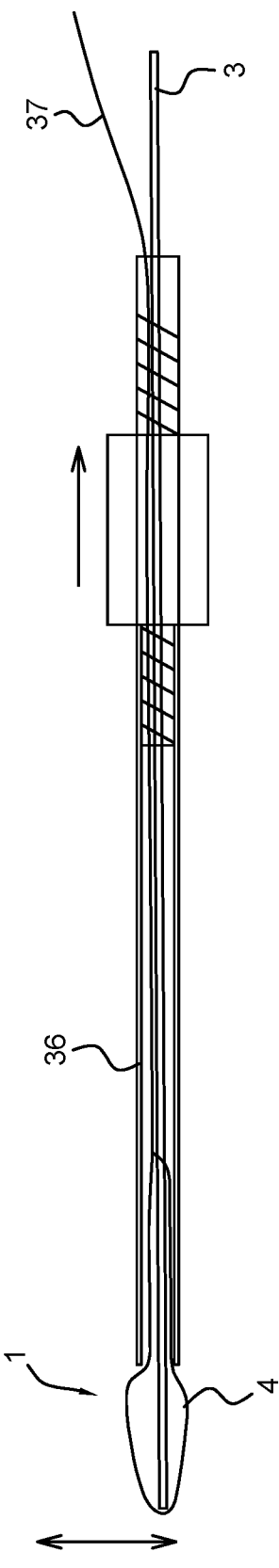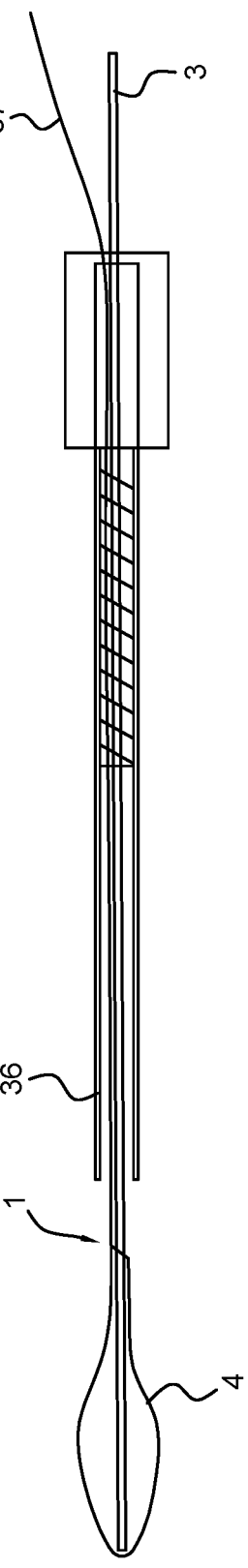

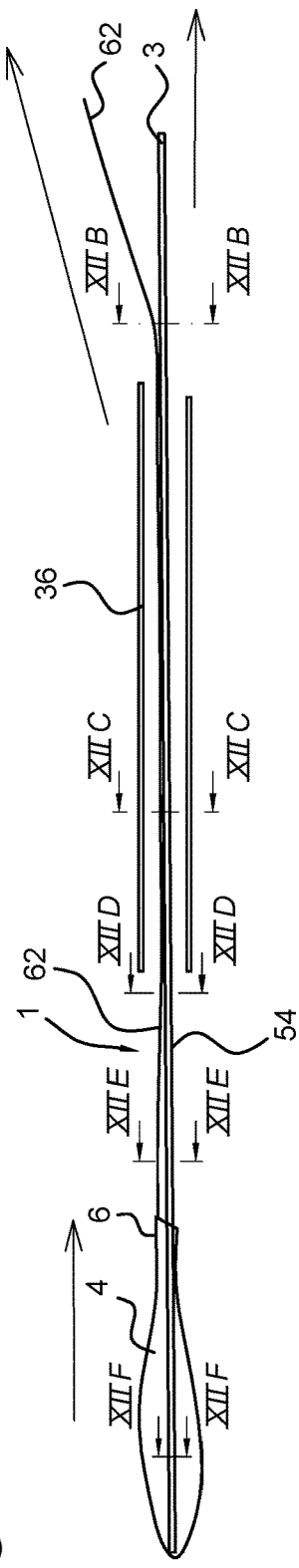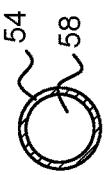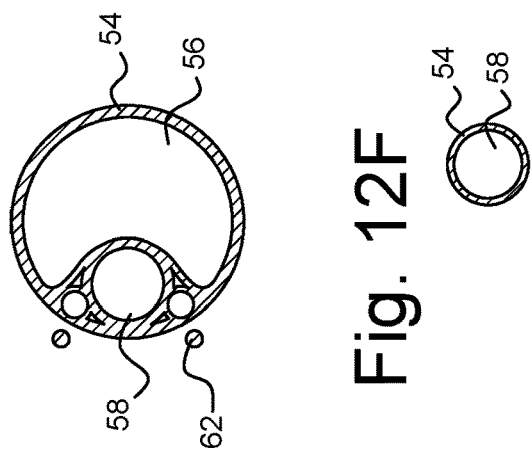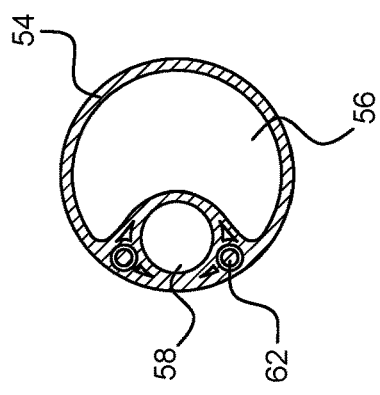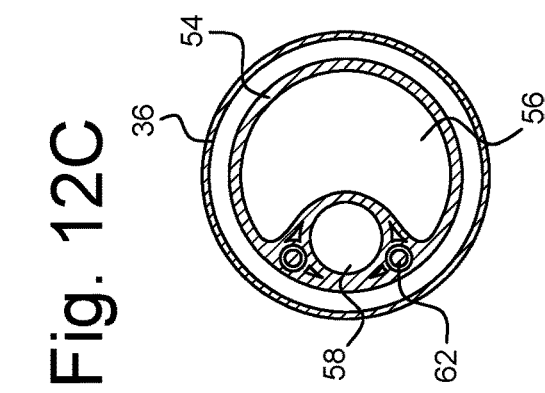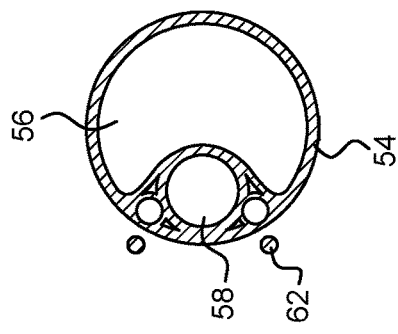

CARDIAC ASSIST DEVICE WITH HIGH FREQUENCY OPERATION

CROSS-REFERENCE TO RELATED APPLICATIONS

The present application is a continuation of International Application No. PCT/NL2022/050193, filed Apr. 7, 2022, which claims the benefit of priority to Dutch Patent Application No. 2028130, filed May 3, 2021, now Dutch Patent No. 2028130, issued Nov. 10, 2022, each of which is incorporated by reference herein in its entirety.

FIELD OF THE INVENTION

The present invention relates generally to circulatory support devices and systems, and more specifically to cardiac assist devices which can be delivered percutaneously into a cardiovascular lumen and are capable of pumping blood at flows high enough to support patients in cardiogenic shock, acute myocardial infarction, acute heart failure or during high risk percutaneous coronary interventions, or other situations requiring hemodynamic support with reduced levels of hemolysis.

BACKGROUND OF THE INVENTION

For patients suffering from cardiogenic shock, or those undergoing high-risk percutaneous coronary interventions (PCI), a patient's heart function may be compromised such that the use of circulatory assist devices may be required to maintain adequate blood flows through the circulatory system. Although there is some variation depending on patient size and condition, circulatory assist devices for patients undergoing high risk PCI typically must produce blood flows of least 3 L/min to maintain adequate circulation, while for patients in cardiogenic shock, a minimum of 5 L/min is generally considered necessary.

The most common types of circulatory assist devices are intra-aortic balloon pumps (IABP), extra-corporeal membrane oxygenation (ECMO) systems, and impeller-based blood pumps. IABP's are catheters having an inflatable balloon which can be placed in the descending aorta and cyclically inflated to displace the blood. ECMO systems include a venous catheter for removing deoxygenated blood from the venous system, an extracorporeal oxygenator and pump, and an arterial catheter for returning the blood to the arterial system, thus bypassing the heart. Impeller pump systems have a rotary impeller that can be placed in a chamber of the heart or in a major vessel and rotated at relatively high speed to propel blood through the circulatory system.

While offering some benefit in increasing blood flow and reducing load on the heart, currently available circulatory assist devices suffer from certain drawbacks. IABP's may not improve flows adequately to support the patient when the heart is significantly compromised, such as during cardiogenic shock. ECMO systems may have higher morbidity associated with multiple catheterizations including bleeding, thrombus, and infection, as well as problems associated with membrane oxygenation including cognitive deficit and stroke. In addition, they increase afterload which is generally regarded as counter-productive. Impeller pump systems, if operated at higher speeds in order to produce higher flows, can result in excessive hemolysis; further, if impeller pumps are made larger to produce higher flows, the profile of such devices can be undesirably large, inhibiting percutaneous delivery, and increasing the risk of injury to cardiovascular structures and/or causing limb ischemia. As a result, current impeller-type pumps which are capable of providing the high flows necessary for patients in cardiogenic shock, are often too large for endovascular delivery thus requiring surgical placement, and further produce undesirable levels of hemolysis.

What are needed, therefore, are circulatory support devices capable of producing blood flows of at least 3 L/min for high-risk PCI procedures, and at least 5 L/min to support patients in cardiogenic shock, which also have a compact delivery profile to allow percutaneous introduction and endovascular placement, have a small size when in operation to reduce space requirements and trauma to cardiovascular structures, and minimize hemolysis and other complications.

BACKGROUND ART

U.S. Pat. No. 5,169,378 describes an intraventricular assist pump having an expandable external chamber and an internal balloon which can be sequentially inflated and deflated to generate a pumping action.

International patent publication WO2008/113785 discloses a device for circulating a body fluid that includes a catheter device which has at least one inlet section for receiving the body fluid at a first location, an outlet section disposed at a distance from the inlet section for discharging the body fluid at a second location disposed at distance from the first location, and a pump device for the directed transport of the body fluid between the inlet section and the outlet section of the catheter device.

International patent publication WO2015/131879 discloses a catheter device for conducting a bodily fluid in a directed manner. The catheter device comprises a sleeve having an internal space, a frame, and at least three openings, wherein the sleeve is configured as a conduit for fluid between the first and second openings. A balloon of a balloon catheter may be placed through a third opening in the sleeve and inflated and deflated to transport bodily fluids through the sleeve.

SUMMARY OF THE INVENTION

The present invention seeks to provide a heart assist device which can be inserted into an operational position easily and is able to provide a heart assist function in an efficient and reliable manner.

According to the present invention, a heart assist device, system, and method are provided which produce high blood flows while having a low device profile for improved endovascular deliverability, less hemolysis, and reduced trauma to cardiovascular structures. The heart assist device may comprise a pumping device positionable in a cardiovascular lumen and comprising a pumping mechanism, an inlet, and an outlet. The pumping device may have a transport state with a delivery profile suitable for insertion through a peripheral blood vessel and may be expandable to an operational state in a cardiovascular lumen which minimizes engagement with cardiovascular tissues during delivery and operation. In the operational state the pumping device is configured to produce blood flows of at least 3 L/min, and preferably at least 5 L/min. At the same time, the pumping device is collapsible into a delivery profile of no more than 18 Fr, and in some embodiments, no more than 14 Fr. Moreover, in some embodiments, the pumping device is capable of producing blood flows of 6-10 L/min or more, either in one or more short bursts or over sustained periods, which may be highly beneficial for cardiogenic shock patients whose organs are in serious distress.

In preferred embodiments, the pumping device comprises an expandable cup having a pumping chamber, and the pumping mechanism comprises a volume displacement member within the pumping chamber. The volume displacement member is configured to cyclically move between a low-volume state and a high-volume state at a frequency significantly higher than the patient's natural heartbeat, preferably 2-10 times higher, and in some embodiments, up to 100 times higher than the natural heartbeat.

The terms "heart assist device" or "pumping device" as used herein are intended to include various types of intracorporeal pumps for use in various cardiovascular lumens, including, without limitation, percutaneous ventricular assist devices (pVAD's), transvalvular pVAD's, and intravascular and intra-ventricular balloon pumps, except as may be stated otherwise with respect to any particular embodiment. Uses within the left side of the heart and arterial system, as well in the right side of the heart and venous system, are contemplated.

A volume displacement member according to the inventions may comprise any of various types of mechanisms capable of displacing a volume of fluid in a cyclical, repeating manner. In a preferred embodiment, the volume displacement member comprises an inflatable balloon which can be inflated with a fluid to the high-volume state and deflated partially or completely to the low-volume state. In other embodiments, a piston, bellows, accordion-style expandable body, or other type of volume displacement member may be used. The volume displacement member will be capable of moving cyclically, at the frequencies disclosed herein, between the low-volume state, in which it occupies a lower portion of the pumping chamber, to a high-volume state, in which it occupies a substantially greater portion of the pumping chamber, thus displacing blood therefrom.

In some embodiments, the pumping device comprises an expandable cup defining a pumping chamber, and a pumping mechanism disposed within the pumping chamber. The expandable cup may have at least one, and preferably a plurality of inflow apertures in a wall thereof which permit blood to flow into the pumping chamber. In addition, an outflow nozzle in communication with the pumping chamber may be coupled to the expandable cup. In certain embodiments, either or both the inflow apertures and the outflow nozzle may include one-way valves.

In preferred embodiments, the pumping mechanism comprises a volume displacement member, which may be an inflatable member such as a balloon. The balloon is preferably configured to be cyclically inflated and deflated at a frequency substantially higher than the patient's natural heartbeat. In some embodiments, the balloon is inflatable from a collapsed configuration to an inflated configuration and is substantially non-distensible beyond the inflated configuration. The expandable cup is configured to be expandable from a low-profile delivery configuration in the transport state to a deployed configuration in the operational state, and is preferably substantially non-distensible beyond the deployed configuration.

In preferred embodiments, the expandable cup will have a maximum diameter in the operational state of less than 25 mm, more preferably less than 18 mm, and in some cases between 3 and 12 mm. In some embodiments, the internal volume of the expandable cup (i.e. pumping chamber volume) in the operational state is between 0.3 and 20 ml, and the volume displacement member may be cyclically alternated between the low-volume and high-volume states at frequencies between 100 and 10,000 beats per minute. In other embodiments, the internal volume of the expandable cup in the operational state is between 1 and 20 ml, and the volume displacement member can be alternated between the low-volume and high-volume states at a frequency of between 100 and 5000 beats per minute. In still other embodiments, the internal volume of the expandable cup in the operational state is between 5 and 10 ml, and the volume displacement member can be alternated between the low volume and high-volume states at a frequency of between 200 and 2000 beats per minute.

It will be appreciated that term "beat" as used herein refers to a cycle of movement of the volume displacement member from the low-volume state to the high-volume state and back again, e.g., a cycle of balloon inflation and deflation. Thus, operating the cardiac assist device at a frequency of, e.g., 1000 beats per minute means that the volume displacement member is cyclically moved between the low-volume and high-volume states 1000 times per minute. These "beats" or "cycles" may or may not be timed synchronously with the natural beats of the patient's heart.

In preferred embodiments, a tubular outflow nozzle is coupled to the expandable cup in communication with the pumping chamber, wherein blood flows through an outflow opening in the pumping chamber into the outflow nozzle. The outflow nozzle may be elongated to as to conduct blood away from the pumping chamber to a cardiovascular location downstream thereof. The outflow nozzle may also include or constitute a one-way valve which allows blood to flow out of the pumping chamber and nozzle and prevents back flow of blood through the nozzle into the pumping chamber. The term "nozzle" as used herein may include tubular structures that have a reduced diameter or constriction relative to the pumping chamber of the expandable cup, or in some cases may refer to a conduit which is not substantially smaller in diameter than the pumping chamber.

In certain embodiments, the expandable cup, the outflow nozzle, the volume displacement member, or a combination thereof, is configured to create a Venturi effect in the blood during operation. In some cases, this is due to the reduced diameter of the outflow nozzle relative to the pumping chamber. A pressure gradient is created between pumping chamber and outflow nozzle which causes blood to flow at a higher rate out of the pumping chamber, which in turn draws more blood into the pumping chamber through the inflow apertures. This supplements the flow created by the volume displacement member such that the actual flows exiting the device exceed what would be achieved solely by the displacement of blood by the volume displacement member. Thus, if the volume displacement member is operating at a frequency F and displaces a volume of blood $V_d$ in each cycle (e.g. each inflation of the balloon), blood flows out of the outflow nozzle at an exit flow rate R, wherein $R > F \cdot V_d$.

In some embodiments, the cup element is configured for placement in the left ventricle (LV) and the outflow nozzle is configured to extend through the aortic valve into the aorta such that blood flows out of the cup into the aortic lumen. The outflow nozzle may have a length selected so that the outlet port in its proximal (downstream) end is disposed in the ascending aorta, in the aortic arch, or in the descending aorta. In order to avoid any flow restrictions resulting from the angle of the aortic arch relative to the left ventricle, the outflow nozzle may be positionable or preshaped at a non-zero angle or curve relative to a longitudinal axis of the expandable cup so as to align the outflow nozzle with the aortic lumen. Preferably, the configuration of the outflow nozzle is selected to minimize disturbance of the flow of blood exiting the pumping chamber, minimizing turbulence and maintaining laminar flow. The outflow nozzle may be flexible so as to pass through the aortic valve and conform to the shape of the aorta with minimal trauma to tissue and to direct the blood flow directly downstream, aligned with the longitudinal axis of the aorta. The exterior of the outflow nozzle may be configured to provide an atraumatic surface against which the aortic valve leaflets can close and seal at least during diastole, and in some cases during systole as well. Other than the outflow nozzle's passage through the aortic valve, the cup element is preferably configured to leave the aortic valve and mitral valve of the heart unobstructed in the operational state.

In preferred embodiments, the cup element may include a self-expanding, resilient support member. The support member preferably comprises a material, geometry, and other structural properties selected to resist diametrical expansion beyond the deployed configuration when the pumping chamber is filled with blood and the balloon is inflated to produce increased pressure in the pumping chamber. Such non-distensibility allows spacing to be maintained between the cup element and the ventricular wall to minimize trauma to heart tissue and also increases pump efficiency. In addition, the support member may be configured to resist collapsing when the pumping chamber is under negative pressure during balloon deflation. At the same time, the support member should be configured to be collapsible or crimpable into the lower profile transport state when subject to sufficient external forces to allow for endovascular delivery and retrieval. In preferred embodiments, the support member may comprise a skeleton of a resilient metal such as nickel-titanium alloy, which may be in the form of expandable woven wires, mesh, basket, or a monolithic tube having an arrangement of openings, slits, or cells which allow expansion in at least one dimension from the transport state to the delivery state.

In embodiments configured for placement in the left ventricle, the support member is preferably configured to extend from within the ventricle to a location in the ascending aorta so as to support the outflow nozzle. Alternatively, a nozzle support member, separate from that of the cup, may be coupled to the outflow nozzle to provide support thereto. The nozzle support member may be coupled directly or indirectly to the cup support member, or it may be unattached thereto. The nozzle support member may be tubular so as to completely surround the outflow nozzle, or it may be partially cylindrical or generally flat so as to extend along a lateral side of the outflow nozzle on one side of the aortic lumen, and may transition along its longitudinal axis from one shape into the others—from generally circumferential to partially cylindrical to generally flat. The proximal (downstream) end of the support member may be shaped and configured to facilitate retrieval of the device, e.g. having a tapered or rounded end. The nozzle support member and/or cup support member may include a retrieval coupling, such as a loop, knob or hook, which may be coupled to or capturable by a retrieval device such as a wire, snare, sheath, or catheter. Alternatively, one or more retrieval wires may be coupled to the end of the support member and configured to remain coupled thereto throughout a procedure, so that, following the procedure, the wire(s) may be pulled to retract the support member, along with the cup and balloon, into a sheath or other capturing means to collapse it into the transport state and withdraw it from the patient.

A blood-impermeable membrane preferably extends over at least a portion of an inner and/or outer surface of the support member. In some embodiments, the support member is embedded within the membrane, or sandwiched between inner and outer membranes. Preferably, the support member/membrane combination is substantially non-distensible in the operational state under pressures of up to 400 mmHg, more preferably up to 800 mmHg or more, within the pumping chamber. The support member and/or membrane may include at least one inflow aperture in communication with the pumping chamber through which blood flows into the chamber from the ventricle during balloon deflation, and an outflow nozzle through which blood is directed from the chamber during balloon inflation. The inflow apertures may each include a one-way valve to allow blood flow into pumping chamber and prevent blood flow out of the chamber through the inflow apertures, which may be formed from the same material as the membrane, or may be a different material that is coupled to membrane by welding, bonding, adhesive, or mechanical fasteners. The outflow nozzle may comprise a polymeric tube of the same polymer as the membrane, or a different polymer, and it may be monolithically formed with membrane, or joined thereto by welding, gluing, or other means.

The heart assist device may further comprise a catheter assembly coupled to the volume displacement member and/or expandable cup and configured to operate the volume displacement member such that it alternates between the low-volume and high-volume states. The catheter assembly and volume displacement member may be permanently attached to the expandable cup, or may comprise a separate subsystem that is removable from the cup, allowing the cup to be placed in the cardiovascular lumen by itself, then inserting the volume displacement member into the cup using the catheter assembly. The catheter assembly will be configured to extend from a location outside the patient through the vascular system to the location of the pumping device, e.g. from a femoral artery in the patient's groin area to the left ventricle via the aorta. The catheter assembly is configured to be coupled to a control unit (described below) located outside the patient.

In inflatable balloon embodiments, the catheter assembly is fluidly coupled to the inflatable balloon and has an inflation lumen for delivering inflation fluid to the balloon. The catheter assembly may be configured to optimize delivery of inflation fluid to enable high frequency inflation of the balloon. Preferably, the inflation lumen has a diameter of at least 1 mm. In specific embodiments, the inflation lumen has a cross sectional flow area of between 1 and 20 mm$^2$, and in some cases between 2 and 7 mm$^2$. Additionally, a first part of the catheter assembly and/or inflation lumen may have a larger diameter than a second part of the catheter assembly/inflation lumen, the second part being closer to the inflatable balloon than the first part. The catheter assembly may also be composed partially or entirely of a relatively stiff material or combination of materials and/or have a wall thickness, e.g. 0.1-0.3 mm, selected to minimize expansion, collapse or distortion of the inflation lumen under the pressure of inflation fluid. The inflation fluid may also be cooled by the control unit, and, in some embodiments, the catheter assembly may have a thermally isolating coating on an exterior thereof to maintain the temperature of the inflation lumen at levels to enhance high velocity flow through the inflation lumen. Optionally, the catheter assembly may further include a guidewire lumen extending axially through it to a guidewire port at the distal end to allow the catheter assembly, along with the cup and balloon, to be slidably advanced over a guidewire to the desired location in the cardiovascular system. The catheter assembly may further include a pressure lumen having an opening at or near the distal end to allow blood pressures in or around the cup to be measured during a procedure. Alternatively, the catheter assembly may include a pressure transducer or other sensor coupled at or near its distal end for such pressure measurement. Other sensors may also be provided on the catheter assembly for sensing cardiovascular or pumping parameters in or around the cup.

The heart assist device of the invention provides a unique combination of a compact structure both in the transport and operational states to improve deliverability while decreasing the potential negative interaction with the heart and blood vessels, yet maintaining a high pumping capacity. Advantageously, the heart assist device is capable of pumping blood at flow rates of at least 3 L/min, preferably 5 L/min or more, without causing undue hemolysis, making it suitable for use with a larger variety of cardiovascular procedures and to address a wider range of patient conditions than known cardiac assist devices. In specific embodiments, by adjusting cup volume, frequency and net volume change of the volume displacement member, and other parameters, flow rates of at least 3 L/min are possible for high-risk PCI support, while for treating cardiogenic shock, flows of at least 5 L/min, preferably at least 6 L/min, and in some embodiments up to 10 L/min or more, are possible.

A heart assist system according to the invention may comprise a heart assist device as described herein, and a control unit coupled thereto which is configured to actuate the volume displacement member at frequencies up to 10 times, and in some embodiments, up to 100 times the patient's natural heartbeat, i.e. frequencies up to 1000 beats per minute, and in some cases 1000 to 10,000 beats per minute.

In embodiments employing an inflatable balloon, the control unit is configured to deliver inflation fluid and regulate pumping parameters to provide the desired high blood flow rates from a very compact pump. The control unit may be configured to deliver selected inflation fluids, including very low viscosity fluids e.g. inert gases such as helium, at pressures and temperatures selected to allow cyclical expansion of the volume displacement member, e.g. an inflatable balloon, at frequencies up to 10 times, and in some embodiments, up to 100 times the patient's natural heartbeat, i.e. frequencies up to 1000 beats per minute, and in some cases 1000 to 10,000 beats per minute.

Preferably, the control unit allows user adjustment or tuning of the frequency of the volume displacement member so that an appropriate frequency can be selected by the user for a particular patient and procedure, or the frequency can be changed during a procedure according to the patient's needs. Additionally, the control unit may allow for adjustment of the volume displaced by the volume displacement member, i.e., its volume in the low-volume state, in the high-volume state, or both.

In another embodiment, the volume change of the volume displacement member is generated by changing the pressure of the volume enclosed by volume displacement member, e.g. an inflatable balloon. This may be achieved by pressurizing and depressurizing the enclosed volume through the connecting inner lumen of the catheter shaft.

In embodiments using an inflatable balloon as a volume displacement member, the control unit may further have an overall system configuration, component layout, fluid circuit design, system volume, and duty cycle selected to enable balloon inflation at such frequencies. In an exemplary embodiment, the control unit compresses a reservoir containing the inflation fluid which is connected to the catheter assembly. In this embodiment, compression or pressurization of the reservoir results in the inflation fluid being delivered to the volume displacement member at the distal end of the catheter.

An exemplary embodiment comprising a safety diaphragm comprises a high pressure source, a low pressure source, and a switching arrangement, connected to the high pressure source, the low pressure source and the catheter assembly, and the switching arrangement is arranged to alternately connect the high pressure source and the low pressure source to a fluid reservoir connected to the catheter assembly. In specific embodiments, the control unit is arranged to connect the high pressure source to the catheter assembly during an inflation time period, and to connect the low pressure source to the catheter assembly during a deflation time period, wherein the inflation time period is shorter than the deflation time period. In preferred configurations, a duty cycle of the inflation time period and the deflation period is between 30% and 80%. In exemplary embodiments, the high pressure source is arranged to provide a maximum pneumatic pressure of at least 300 mbar, and an evacuation pressure of less than −100 mbar, relative to atmospheric pressure. In some embodiments, the control unit is configured to pressurize the fluid in the reservoir to a maximum pressure of at least 100 mmHg, and a minimum pressure of less than −50 mmHg, and preferably a maximum pressure of at least 200 mmHg and a minimum pressure less than −200 mmHg relative to atmospheric pressure.

The invention further provides a method of providing cardiac assist to a patient which includes the steps of— delivering a pumping device in a lower-profile transport state through a peripheral blood vessel into a cardiovascular lumen;

expanding an expandable cup of the pumping device to an operational state in the cardiovascular lumen, the expandable cup having a pumping chamber in an interior thereof and at least one inflow aperture and at least one outflow nozzle in communication with the pumping chamber; and cyclically alternating a volume displacement member disposed in the pumping chamber between a low-volume state and a high-volume state to allow blood to flow into the pumping chamber through an inflow aperture and to direct blood out of the pumping chamber through an outflow nozzle;

wherein the volume displacement member is cyclically alternated between the low-volume state and the high-volume state at a frequency of 100 to 10,000 beats per minute.

In another embodiment, a method for providing cardiac assist to a patient's heart comprises— delivering a pumping device in a transport state through a peripheral blood vessel into a cardiovascular lumen;

expanding an expandable cup of the pumping device to an operational state in the cardiovascular lumen, the expandable cup having a pumping chamber in an interior thereof and at least one inflow aperture and at least one outflow nozzle in communication with the pumping chamber; and cyclically alternating a volume displacement member disposed in the pumping chamber between a low-volume state and a high-volume state to allow blood to flow into the pumping chamber through an inflow aperture and to direct blood out of the pumping chamber through an outflow nozzle so as to produce a blood flow of at least 5 L/min;
wherein the expandable cup has a maximum volume of less than 20 ml in the operational state.

In specific embodiments, the expandable cup has a maximum volume of less than 10 ml, and more preferably less than 5 ml.

In still another embodiment, a method of providing cardiac assist to a patient comprises—
delivering a pumping device in a transport state through a peripheral blood vessel into a cardiovascular lumen;
expanding an expandable cup of the pumping device to an operational state in the cardiovascular lumen, the expandable cup having a pumping chamber in an interior thereof and at least one inflow aperture and an outflow nozzle in communication with the pumping chamber; and
cyclically alternating a volume displacement member disposed in the pumping chamber between a low-volume state and a high-volume state to allow blood to flow into the pumping chamber through the inflow aperture and to direct blood out of the pumping chamber through the outflow nozzle so as to produce a blood flow of at least 5 L/min;
wherein the expandable cup has a delivery profile in the transport state of less than 18 Fr.

Preferably, the expandable cup has a delivery profile in the transport state of 14 Fr or less, and more preferably 12 Fr or less.

In yet another embodiment, a method of providing cardiac assist according to the invention comprises:
delivering a pumping device in a transport state through a peripheral blood vessel into a left ventricle of the heart, the pumping device having a delivery profile no more than 14 Fr in the transport state;
expanding at least a portion of the pumping device into an operational state in the left ventricle, the pumping device having a pumping mechanism, an inlet, and an outlet, wherein the outlet is positioned in a lumen of an aorta downstream of the left ventricle; and
operating the pumping mechanism to allow blood to flow into the inlet and to direct blood out of the outlet at a flow rate of at least 5 L/min.

In other embodiments, lower flows may be achieved with lower profile devices. In some embodiments, the pumping device produces at least 3 L/min and the delivery profile of the pumping device in the transport state is no more than 12 Fr, more preferably no more than 10 Fr, and desirably no more than 8 Fr.

In another embodiment, a method of providing cardiac assist to a patient's heart comprises:
delivering a pumping device in a transport state through a peripheral blood vessel into a cardiovascular lumen;
expanding at least a portion of the pumping device to an operational state in the cardiovascular lumen, the pumping device having a pumping mechanism, an inlet, and an outlet; and
operating the pumping mechanism such that blood flows into the inlet and flows out of the outlet at a flow rate of at least 5 L/min;
wherein red blood cells in said blood are subject to maximum shear stresses of less than 400 Pa between the inlet and the outlet.

In yet another embodiment, a method of providing cardiac assist to a patient's heart comprises:
delivering a pumping device in a transport state through a peripheral blood vessel into a cardiovascular lumen;
expanding at least a portion of the pumping device to an operational state in the cardiovascular lumen, the pumping device having a pumping mechanism, an inlet, and an outflow nozzle; and
cyclically moving a volume displacement member disposed inside the pumping chamber between a low-volume state and a high-volume state at a frequency F, wherein the volume displacement member displaces a volume of blood $V_d$ from the pumping chamber during each cycle; and
wherein blood exits the outflow nozzle at an exit flow rate R, where $R > F \cdot V_d$.

In any of the methods of the invention, the pumping device may comprise a heart assist device according to any of the embodiments described herein. In preferred embodiments, the volume displacement member comprises an inflatable balloon which is cyclically alternated between the low-volume state and the high-volume state by cyclically inflating and deflating the balloon, either partially or entirely. In addition, the pumping device may be part of a heart assist system including a control unit as described elsewhere herein.

Other aspects of the nature and advantages of the invention will become apparent from the following detailed description taken in conjunction with the drawings.

SHORT DESCRIPTION OF DRAWINGS

The present invention will be discussed in more detail below, with reference to the attached drawings, in which FIGS. 1A and 1B show partial side views of an embodiment of the heart assist device according to the present invention, in which the inflatable balloon of the heart assist device is inflated and deflated, respectively.

FIG. 2 shows a schematic view of the heart assist device according to an embodiment of the present invention.

FIGS. 9A-C are side elevational views showing a heart assist device according to the invention placed in a delivery sheath in a transport state, partially deployed state, and operational state, respectively.

Figure 10A:
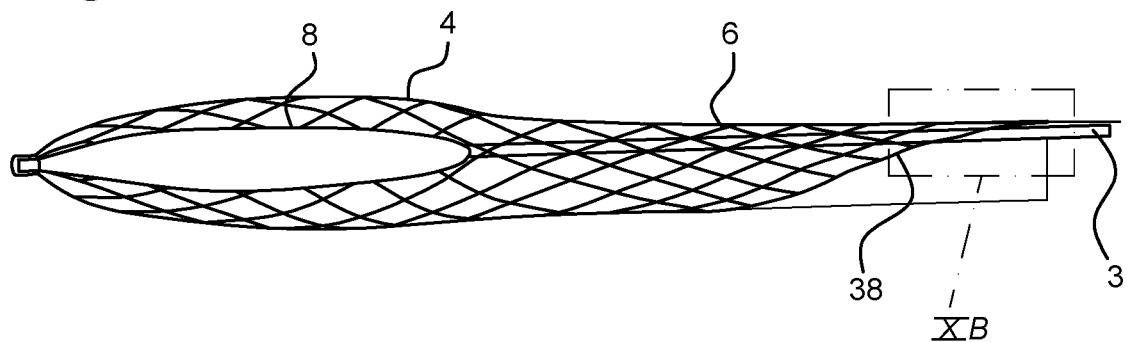

FIG. 10A is a side elevational view of an expandable cup in a heart assist device according to the invention in a further embodiment thereof.

Figure 10B:
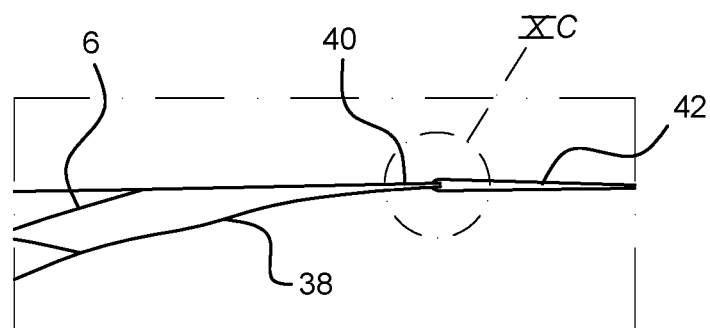
Figure 10C:
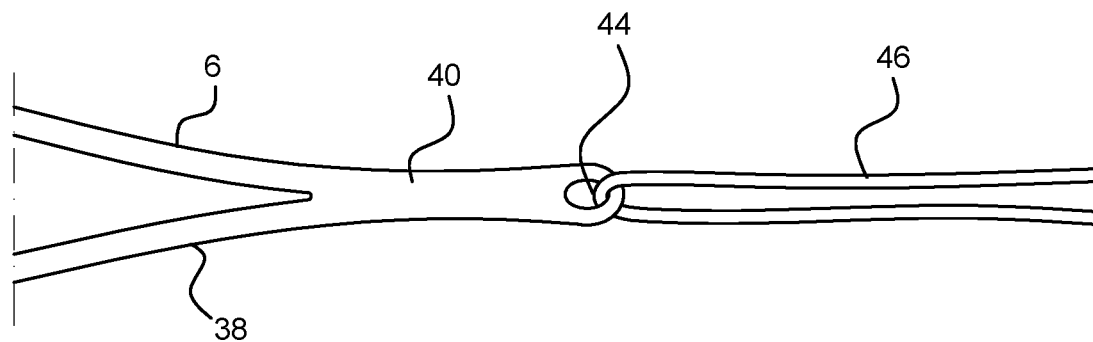

FIGS. 10B and 10C are close-up views of a proximal end of an outflow nozzle of the heart assist device of FIG. 10a in two different embodiments thereof.

Figure 11A:
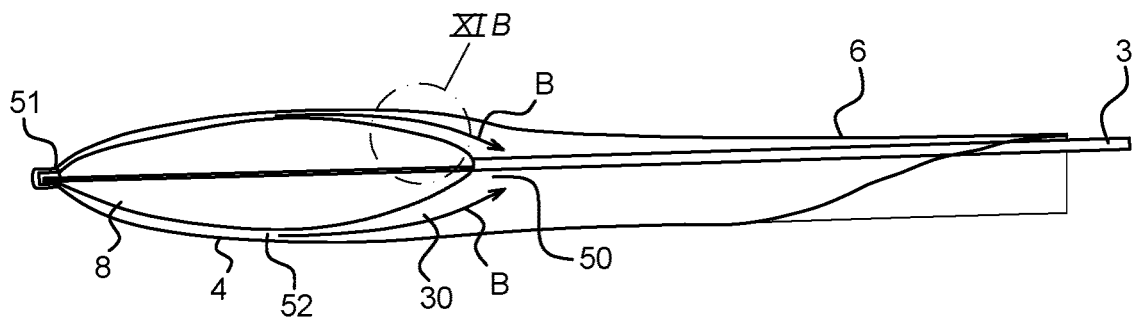

FIG. 11A is a side elevational view of a cardiac assist device of the invention showing the flow of blood in an expandable cup thereof.

Figure 11B:
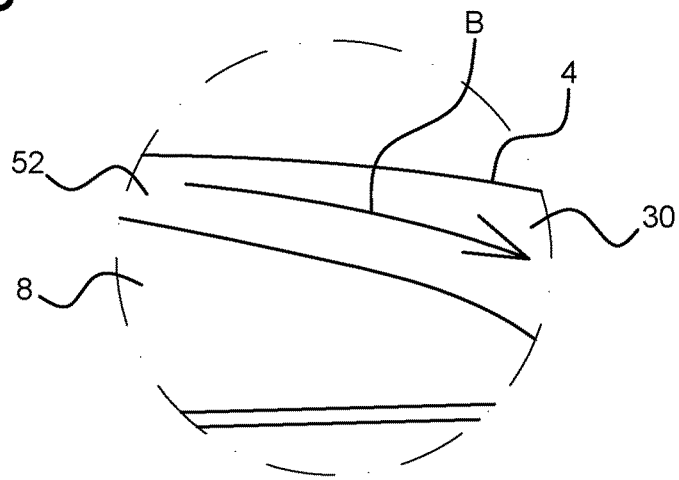

FIG. 11B is a magnified view of a portion of the expandable cup in the cardiac assist device of FIG. 11A.

Figure 11C:
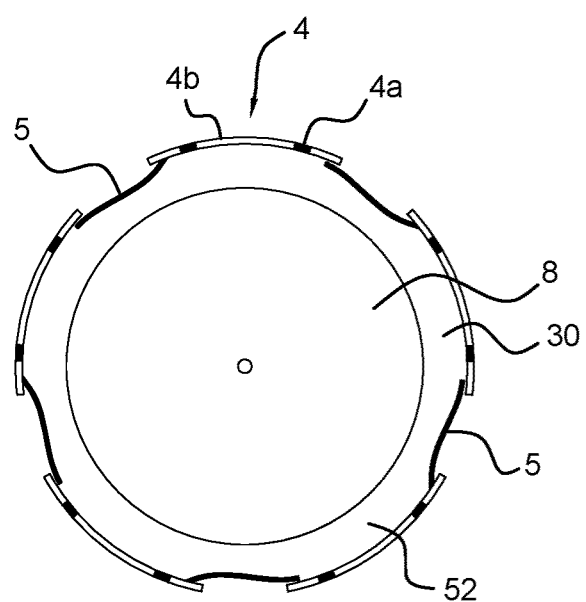
Figure 11D:
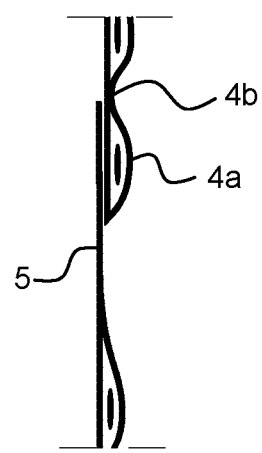

FIG. 11C is a transverse cross-section and FIG. 11D a partial wall cross-section of the expandable cup in the cardiac assist device of FIG. 11A.

FIG. 12A is a side elevational schematic of a cardiac assist device according to the invention placed through a delivery sheath.

FIGS. 12B-F are transverse cross-sections of the cardiac assist device of FIG. 12A at various points along the length thereof.

DESCRIPTION OF EMBODIMENTS

The present invention provides an intra-lumen cardiac assist device, system, and method that are effective in supporting blood circulation in a patient. The cardiac assist device according to the present invention embodiments can function to provide circulatory assistance in a patient by pumping blood from a cardiovascular lumen at higher flow rates, reduced hemolysis, and improved deliverability as compared to known devices. "Cardiovascular lumen" as used herein includes vascular lumens in either the arterial or venous systems, cardiac chambers such as the left or right ventricular or atrial chambers, or the interior of any other organ or vessel in the cardiovascular system.

As shown in the side views of FIGS. 1A and 1B, and the schematic view of FIG. 2, a heart assist system 100 according to the invention includes a heart assist device (or pumping device) 1 and a control unit 2. Heart assist device 1 comprises, an expandable cup 4 having an internal pumping chamber 30, a plurality of inflow apertures 5 and an outflow nozzle 6 in communication with the pumping chamber 30, a volume displacement member 8, positioned within the pumping chamber 30 inside the expandable cup 4, and a catheter assembly 3 connected to the volume displacement member 8 during operation. Volume displacement member 8 is cyclically movable between a low-volume state and a high-volume state. In this embodiment, volume displacement member 8 comprises an inflatable balloon which is inflatable to the high-volume state and deflatable to the low-volume state. Control unit 2 is connected to the catheter assembly 3 and supplies an inflation fluid thereto for inflation of balloon 8.

It will be understood that, although volume displacement member 8 may be shown and described as an inflatable balloon in the various exemplary embodiments disclosed herein, other types of volume displacement members may be substituted for such a balloon without departing from the scope of the invention.

It is noted that the expandable cup 4 has a low-profile transport state configured for endovascular delivery, and a larger-profile operational state, the operational state being shown in the FIGS. 1A and 1B. The inflow apertures 5 are e.g. provided with one-way inflow valves, and the outflow nozzle 6 may be provided with a one-way outflow valve 7, further described below.

In the present invention embodiments, the control unit 2 is arranged to operate the inflatable balloon 8 with a frequency of more than 100 beats per minute, bpm. The inflatable balloon 8 is deflated via the catheter assembly 3 to allow blood to enter the pumping chamber 30 of the expandable cup via the inflow apertures 5 (totally deflated state 8B shown in dotted lines in FIG. 1B), and subsequently the inflatable balloon 8 is inflated thereby expelling blood out of the outflow nozzle 6 (totally inflated state 8A shown in dotted lines in FIG. 1A). Having a high frequency of deflating and inflating (>100 bpm) allows to have a smaller pumping volume (internal volume of expandable cup 4) and hence smaller dimensions and improved deliverability of the heart assist device as compared to prior art heart assist devices, yet maintain a sufficient high throughput to effectively operate as a heart assist device.

In a group of embodiments, an internal volume of the expandable cup 4 in operational state is between 0.3 and 20 ml. This allows to design the heart assist device 1 with minimal dimensions, making positioning the heart assist device 1 in e.g. a left ventricle of a patient's heart easier. Also, transportation of the heart assist device in transport state (with the entire expandable cup 4 folded over the inflatable balloon 8 and end of the catheter assembly 3) through patient's arteries is then very well possible.

The control unit 2 can be arranged to operate the inflatable balloon 8 with a predetermined frequency of more than 100 bpm to obtain a sufficient flow of blood through the heart assist device 1 when using the higher range of volume indicated (20 ml), or with a higher frequency, even up to 10000 bpm, when using the lower range of volume indicated (0.3 ml).

In an exemplary embodiment, the internal volume of the expandable cup 4 in operational state is between 1 and 20 ml, and the control unit 2 is arranged to operate the inflatable balloon with a frequency of between 100 and 5000 beats per minute. This sufficiently high frequency of operation in combination with a relatively low pumping volume allows the heart assist device to maintain a sufficient blood flow rate.

In a further exemplary embodiment, the internal volume of the expandable cup 4 in operational state is between 5 and 10 ml, and the control unit 2 is arranged to operate the inflatable balloon with a frequency of between 200 and 1000 beats per minute. The smaller size and associated range of operational frequency allows a sufficient assisted flow of blood to provide proper function of the heart assist device 1.

The dimensions of the heart assist device 1, mainly the internal volume of the expandable cup 4 in cooperation with the size and position of the inflatable balloon 8 (in combination with the extent to which the inflatable balloon 8 is inflated by the control unit 2) determines the (maximum) stroke volume. Combined with the frequency this determines the blood flow through the heart assist device 1.

An internal volume of 20 ml can e.g. be obtained with a maximum outer diameter of the heart assist device 1 of 25 mm. Lower volumes may be obtained by reducing the diameter to a value of e.g. 12 mm, more preferably 10 mm, which can be offset by a higher pumping frequency of e.g. 600 bpm to obtain a sufficient high blood flow through the heart assist device 1. Even smaller heart assist devices 1 may be obtained, e.g. having an internal volume of 1 ml or even 0.3 ml, wherein sufficient flow of blood is maintained by increasing the pumping frequency to 2000 bpm, or even 5000 or 10000 bpm. Diameter of the heart assist device 1 may then be between 0.3 and 10 mm.

A lower pumping frequency may be advantageous in view of prolonged operational life, especially of the internal balloon 8. Exemplary embodiments in this group have a pumping frequency of between 200 and 600 bpm and an internal volume of between 5 and 20 ml. A higher pumping frequency may be advantageous with respect to external dimensions of the heart assist device 1 (both in transport state and in operational state), e.g. a pumping frequency in the range of 600 to 5000 or even 10000 bpm, in combination with a range of internal volume of between 0.3 and 5 ml.

The control unit 2 may also be arranged to change the pumping frequency, e.g. by operator input/adjustment or by automatic control using sensor data and a control algorithm. The actual blood flow through the heart assist device 1 can then (also) be controlled using only the pumping frequency as controlling parameter.

Figure 3A:
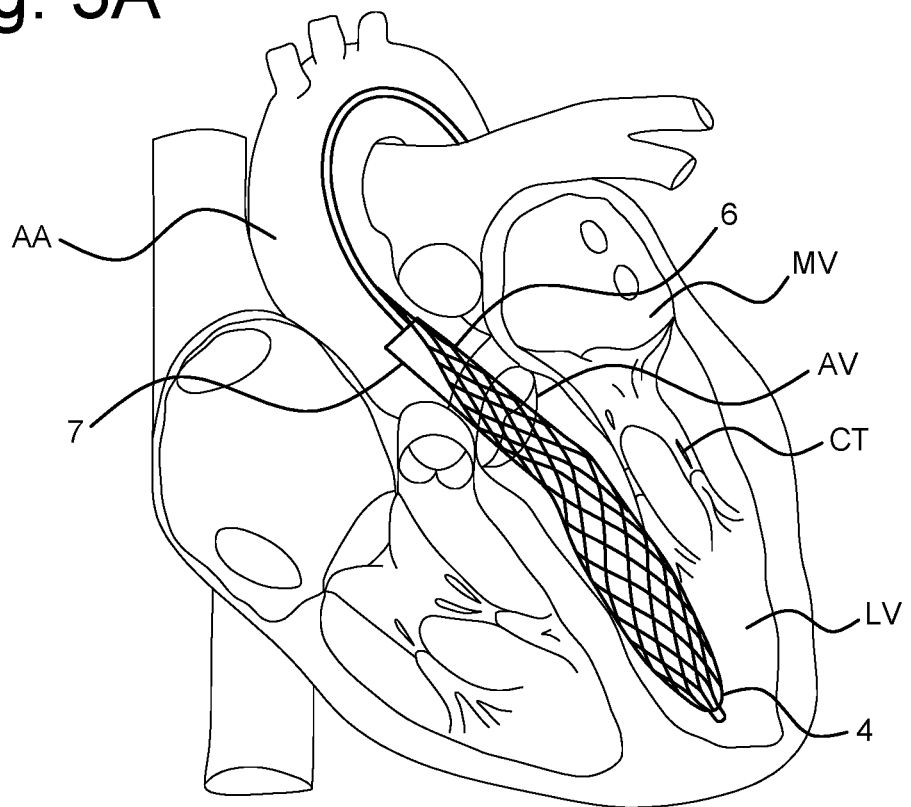
FIG. 3A shows a heart assist device according to a further embodiment of the present invention positioned in a left ventricle of a patient's heart.
Figure 3B:
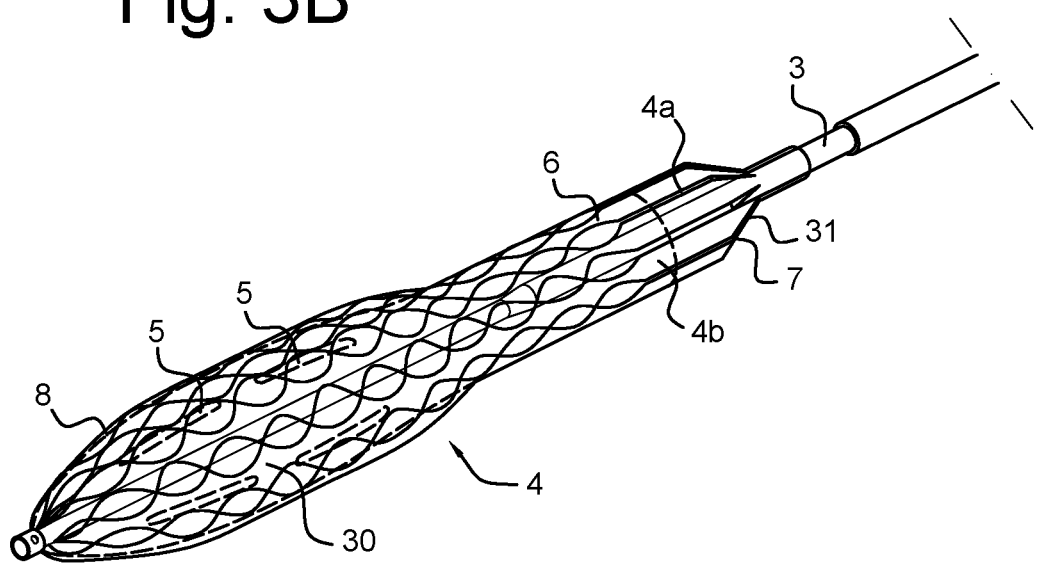
FIG. 3B illustrates a perspective view of the heart assist device of FIG. 3A.

FIG. 3B shows a perspective view of a heart assist device 1 according to a further exemplary embodiment of the present invention, showing details of the expandable cup 4, inflatable balloon 8 and part of the catheter assembly 3. FIG. 3A shows heart assist device 1 positioned in a left ventricle LV of a patient's heart. In this group of embodiments, the expandable cup 4 comprises a support structure (or skeleton) 4a of a material which is expandable from the low-profile transport state to the expanded operational state, is preferably non-distensible beyond its size in the operational state, and remains collapsible for withdrawal. Expandable cup 4 further comprises an outer wall 4b of semi-rigid or flexible material connected to, encasing, or extending over the outer surface of the support structure 4a. In addition to or instead of outer wall 4b, an inner wall (not shown) may be provided on the inner side of support structure 4a, which may have similar properties as outer wall 4b, and be composed of the same or different materials. The support structure 4a can be embodied using e.g. resilient metal wires woven or formed in a mesh, a laser-cut tube, tubular basket or stent-like structure, a mesh or series of ribs or fibers made of a non-distensible polymeric material such as nylon, or inflatable tubing of nylon or other polymer. In preferred embodiments, support structure 4a is a monolithic tube or basket-like structure of a resilient metal, e.g. nickel-titanium alloy (Nitinol), cobalt-chrome, Chromoly, or stainless steel, comprised of a plurality of struts or cells arranged in a radially-expandable geometry. Preferably, support structure 4a is collapsible into the low-profile operation state and resiliently biased into the expanded operational state. Support structure 4a may further be embedded within either the outer wall 4b or inner wall, or sandwiched between the inner and outer walls.

The expandable cup 4 is preferably semi-rigid in the operational state due to either support structure 4a and outer wall 4b (and/or the inner wall, if provided), or a combination of any of those elements, even during operation when the inflatable balloon 8 is inflated and deflated in rapid sequence inside the expandable cup 4, increasing fluid pressures therein. By "semi-rigid", it is meant that, when balloon 8 is inflated, increasing pressures in the pumping chamber 30, the expandable cup 4 is substantially non-distensible, or distensible a known or predictable amount, beyond the diameter to which it expands in the operational state. This allows expandable cup 4 to be appropriately sized so as to limit excessive engagement or forces on the ventricular wall. Further expandable cup 4, in the operational state, is configured to resist contraction or collapsing under negative pressure within the pumping chamber 30. Preferably, expandable cup 4 will not expand more than about 3% or 0.5 mm in diameter under internal fluid pressures up to 500 mmHg, while any decrease in diameter should be no more than 2% or 0.3 mm during deflation. Expandable cup may still have the flexibility to deform into a non-circular shape or to bend so as to conform to the cardiovascular lumen (e.g. left ventricle and aorta) and, if subject to sufficient force directed radially inward, will be collapsible into the transport state for removal.

In the operational state the expandable cup 4 directs the kinetic energy provided to the blood by the inflatable balloon 8. The inflatable balloon 8 is the active component of the heart assist device 1 and is cyclically inflated and deflated. During inflation, the inflatable balloon 8 expands and displaces volume, thereby also creating kinetic energy which increases the velocity of the displaced blood and as a result decreases its viscosity. To direct the accelerated blood towards the aortic system the expandable cup 4 (comprising a membrane/outer wall 4b, inflow valves provided in the inflow apertures 5, outflow valve 7 provided in the outflow nozzle 6, and the support structure 4a) directs the volume displacement radially and/or in a downstream direction, i.e. towards the outflow nozzle 6, which is e.g. placed through the aortic valve or alternatively placed in the ventricle and directed at the aortic valve. During deflation, the outflow valve 7 closes, to prevent backflow, while the inflow valves open, to allow inflow of fresh blood from the surrounding lumen into the internal volume of expandable cup 4.

When the expandable cup is placed in the LV, as shown in FIG. 3A, the outflow nozzle 6 will direct the fluid out of the heart. In preferred embodiments, the outflow nozzle 6 extends from cup 4 across the aortic valve into the ascending aorta. Outflow nozzle 6 has an outlet 31 at its proximal (downstream) end with an outflow valve 7, which, in various embodiments, is configured to be positioned in the ascending aorta AA, in the aortic arch, or in the descending aorta. In right heart embodiments, outflow nozzle 6 may be configured to extend from expandable cup 4, positioned in the right atrium or right ventricle, through the pulmonary valve into the pulmonary artery. For the outflow valve 7 to be optimal in performance the outflow resistance is as low as possible, while being fast in opening and closing, with a good sealing capacity in the closed position. For this the inner diameter of the nozzle 6 and outflow valve 7 are dependent on the flow (velocity) coming out of the device, which is preferably below 4 m/s for a device pumping around 5 L/min in pulsatile fashion. In such embodiments, the outflow nozzle 6 including outflow valve 7 has an inner diameter of about 5-17 mm, and preferably about 12 mm or less.

As shown in FIGS. 5A-5B and 6A-6B, outflow nozzle 6 comprises a supportive structure 32 and a dynamic structure 34. The supportive structure 32 may be a monolithic extension of the support structure (skeleton) 4a of the cup, or a separate structure which may be coupled directly or indirectly to the support structure 4a of the cup. The dynamic structure 34 should be connected to the supportive structure 32 at least in the distal region (nearer the ventricle), or in multiple locations, e.g. in the distal region and across the back-bone on one or multiple lines. In some embodiments the entire length of the dynamic structure 34 all the way to its outflow end is attached to the supportive structure 32. The supportive structure 32 may be tubular to surround the dynamic structure 34 over all or a portion of its length, or it may be only partially tubular, e.g. in a more distal region closer to the ventricle, with the remaining portion being a partial cylinder or elongated, flat structure configured to be positioned on only one side of the aortic lumen. In some embodiments the supportive structure 32 progressively transitions from cylindrical to flat. The dynamic structure 34 may be a flexible polymer, and in some embodiments, the same as the membrane of the cup. The dynamic structure 34 is movable between an open configuration in which blood may flow out of outflow nozzle 6 (shown in FIGS. 6A-B), and a closed configuration in which blood is blocked from flowing back into outflow nozzle 6 when balloon 8 is deflating and creating negative pressure in pumping chamber 30 (shown in FIGS. 5A-B). The dynamic structure 34 itself may have progressive stiffness or radial strength. For example, it could be made from a tube with a stiffer inflow end than the outflow or valving end 31 of the structure. Progressive stiffness may be provided by changing wall thickness, material types or material durometers along the length of the dynamic structure. The length of the dynamic structure is related to the diameter and is preferably 0.5-3.5 cm, more preferably 2 cm, long, 8-14 mm, preferably 12 mm, in diameter, with a wall thickness of 20-120 mu, preferably 80 mu. As illustrated in FIGS. 5A-B and 6A-B, outflow valve 7 may comprise a portion of the tubular outflow nozzle 6 near the outlet end 31, configured to collapse and seal when the pressures within it are exceeded by those outside it. Alternatively, the outflow valve 7 could be a wind-sock valve, duckbill valve, flap valve, or multi-leaflet valve mounted to the outlet end 31 of outflow nozzle 6.

In certain embodiments, the expandable cup 4, the outflow nozzle 6, the volume displacement member 8, or a combination thereof, may be configured to create a Venturi effect in the blood during operation. The increasing volume of the displacement member (e.g. by inflation in the case of an inflatable volume displacement member such as an inflatable balloon) imparts kinetic energy and velocity onto the displaced blood. The moving blood will drag along surrounding blood in its wake, creating a Venturi effect that is in addition to the displacement of the blood from the pumping chamber by the volume increase of the volume displacement member. Furthermore, in some embodiments the outflow nozzle 6 has a reduced diameter relative to that of the pumping chamber 30 such that blood flowing out of the pumping chamber 30 accelerates, causing a pressure drop. In exemplary embodiments, the pumping chamber 30 diameter may range from A to B mm, while nozzle 6 inner diameter may range from C to D mm, resulting in a ratio of the inner diameter of the outflow nozzle 6 to that of the pumping chamber 30 of between X and Y. The pressure gradient between pumping chamber and outflow nozzle causes blood to flow at a higher rate out of the pumping chamber, which in turn draws more blood into the pumping chamber through the inlets. This supplements the flow created by the volume displacement member such that the actual flows exiting the device exceed what would be achieved solely by the displacement of blood by the volume displacement member. Thus, if the volume displacement member is operating at a frequency F and displaces a volume of blood $V_d$ in each cycle (e.g., each inflation of the balloon), blood flows out of the outflow nozzle at an exit flow rate R, wherein $R > F \cdot V_d$. Such exit flow rates can be as high as 40-80% larger than the flow rate produced solely by volume displacement, or more.

FIGS. 7A-D and 8A-D illustrate inflow valves 5 of expandable cup 4 in closed and open configurations, respectively. Valves 5 may comprise elongated leaflets coupled to the inner or outer wall of cup 4 and extending over elongated inlet openings in the cup wall. In some embodiments, the leaflets are formed from the same material as the membrane of the inner or outer wall of the cup 4. As shown in FIGS. 7A-D, as balloon 8 inflates, inflow valves 5 are in a closed configuration which blocks blood from flowing out of pumping chamber 30 as pressure in pumping chamber 30 increases. Outflow valve 7, shown in FIGS. 7C-D, opens, allowing blood to exit. As shown in FIGS. 30 8A-D. when balloon 8 deflates, pressure in pumping chamber 30 decreases, causing outflow valve 7 to close. When the pressure in pumping chamber 30 becomes low enough relative to the surrounding pressure, inflow valves 5 open, allowing blood to flow into pumping chamber 30. Inflow valves 5 are designed to have a low resistance during the inflow of the device, while having a high sealing capacity during the ejection. To allow for high actuation frequency, the inflow valves 5 should be able to have a fast response time, both for opening and closing. To achieve this, the total inflow area of valves 5 should be at least 50 mm2, preferably 200-500 mm2, which could be within a single valve, or distributed over 2-500 valves, preferably between 10 and 50 valves. Preferably, valve geometry, size, number and configuration will be selected to minimize resistance to blood flow into pumping chamber 30. The valves may be formed of a flexible, impermeable polymer, fabric, or tissue. For high flexibility the durometer of the leaflets may be lower compared to the cup. The leaflets will be organized such that inflow of blood is as laminar as possible. This can be achieved by placing the valves in one direction, e.g. horizontal-, vertical-, or oblique plane, or a combination thereof.

The support structure 4a is built out of material that can be folded or collapsed into a transport state having small profile for delivery, and expanded to a larger operational state with a consistent shape which is resistant to high interior pressures, preferably being substantially non-distensible at interior pressures up to 400 mm Hg (range 200-600 mmHg). The support structure 4a can e.g. be folded to fit within a 2-8 mm, more preferably 3-5 mm, lumen of a delivery sheath, for introduction into the desired vascular lumen. When in position the support structure 4a is expanded to it operational state with a diameter of e.g. 18 mm (in a preferred range of between 5-24 mm). When expanded, the support structure 4a will prevent collapse of the membrane/outer wall 4b at negative pressures as low as −50 mmHg (preferred range from −10 to −100 mmHg), while during inflation the pressure increase of e.g. +250 mmHg (preferred range from 100-600 mmHg) does not result in an increase of the diameter of the expandable cup 4. The transport state, and the operational state including the inflation and deflation phases will be discussed below.

In the transport state, the support structure 4a is configured such that the maximal stretch for deformation of the material is higher than the eventual stretch on the material during crimping. The combination of a small cup size and volume, low thickness of the cup membrane (preferably 0.01-0.15 mm) and support structure 4a (preferably 0.05-0.3 mm), and low profile shaft of the inflatable balloon (preferably 2.0-3.5 mm), make it possible to have a low crimp profile in the transport state (preferably 8 Fr-18 Fr), while maintaining a high pump capacity (preferably 2 L/min-9 L/min). By varying these parameters, the device can be adapted to a particular clinical need. A preferred configuration for the setting of cardiogenic shock has a delivery profile of 18 Fr or less, more preferably 14 Fr or less, and produces blood flows of at least 6 L/min. For use in high-risk PCI, a delivery profile of 9 Fr or less and producing blood flows of at least 4 L/min is preferred.

In the transport state the device needs to remain flexible enough to pass challenging anatomical variations in the vasculature. For this the support structure 4a should be flexible, for example by having a low wall thickness, e.g. 0.15-0.25 mm in preferred configurations. Furthermore, the design of the support structure 4a needs to be configured to be collapsed or crimped into the transport state without damage that might weaken or fracture the support structure 4a. This can be achieved by selecting materials such as a nickel-titanium alloys which are less susceptible to microfractures, and by designing support structure 4a to minimize microfractures. Importantly, membrane selection is important in determining skeleton material and geometry—e.g., the skeleton should not stretch the membrane material beyond the yield point for plastic deformation, which would compromise the effectiveness of the membrane. The skeleton 4a may comprise a woven wire mesh, or may be formed from a monolithic tube into a plurality of struts in a closed or open cell configuration. Construction of the support structure 4a may be accomplished using super elastic Nitinol, with a heat setting to 35 degrees Celsius. As an alternative, the cup can be made of inflatable struts, e.g. from nylon material, that can be pressurized (e.g. using a fluid) to provide a shape consistency to the outer wall 4b. In one example, the support member/skeleton 4a has a diamond cell design with 4.2 mm struts, which in the expanded state is about 6 mm long and in the collapsed (transport) state 8 mm long, resulting in 100% stretch. In one example, the membrane comprises a TPU like technothane, Pellathane, or Tecothane in a durometer of approximately 72D, which allows these stresses without plastic deformation.

The operational or expanded state the cup is designed not to obstruct native blood flow in the cardiovascular lumen in which it is positioned. When used in the left ventricle LV, as shown in FIG. 3A, the size and shape of the cup 4 in the operational state (expanded) is such that it leaves maximal room for the native blood flow into and out of the left ventricle. There should be no obstruction during inflow via the mitral valve MV, and during the outflow the obstruction of the aortic valve is minimized so that blood can flow out of ventricle around outflow nozzle 6. Preferably, outflow nozzle 6 is configured to extend through the aortic valve AV and allow the aortic valve leaflets to seal against its exterior surface during diastole. Disruption of the mitral valve MV, chordae tendinae CT, papillary muscles, or other structures of the ventricle is also minimized. Furthermore, cup 4 may have a hydrodynamic bullet/ellipsoid or cigar-like shape which prevents compartmentalization of the flow inside the heart. By maintaining the native blood flow there will be no areas of stagnant flow. Hence, with a cup diameter less than 18 mm, preferably less than 15 mm, with a length of less than 60 mm (not including the nozzle 6), in its expanded shape, the hydrodynamic shape of the cup, as well as the distribution of the inflow valves will help to reduce the chance of intra ventricular thrombosis formation. Additionally, given the angle of the aortic valve relative to the axis of the left ventricular lumen, the heart assist device 1 may have a flexible, curved or angulated attachment of the outflow nozzle 6 to the main body of the cup 4 to decrease resistance and while maintaining laminar flow in the outflow of blood.

In the operational state the surface of the cup 4 is preferably smooth to allow for contact with the tissue without damaging it and to prevent areas of thrombus formation. The overall smoothness is achieved by capturing the support structure 4a/skeleton between 2 membranes or layers of polymers in outer wall 4b. These layers may be connected to form one layer in which the skeleton is embedded. The final effect is preferably a fully covered support structure 4a in both the interior and exterior of the cup 4 and nozzle 6. Usually polymer layers are smooth enough, although an additional hydrophilic coating may be added for additional smoothness. Anti-thrombotic coatings may also be employed to reduce clot formation. Outflow nozzle 6 may further have a smooth outer surface configured to allow the aortic valve leaflets to seal against the nozzle surface without trauma.

During deflation of the balloon, the cup preferably maintains its size and shape with limited to no deformation. The support structure 4a, e.g. nitinol skeleton, in combination with the membrane(s) impart a radial strength to the cup to resist such deformation. The radial strength of the cup, i.e. of the support structure 4a and the outer wall membrane 4b combined, needs to withstand the pressure gradient between the ventricle and pumping chamber 30 during the inflow of blood. The magnitude of this gradient depends on the inflow area of the inflow valves (resistance) and the speed and volume of the balloon deflation. In one embodiment, the radial strength is provided by the material properties of the membrane, e.g. tecothane 72D, in a 60$mu$ layer, combined with a diamond or hexagon shaped cell design of a nitinol skeleton having a 0.2 mm wall thickness. By adhesion of the membrane to the support structure 4a, higher radial stiffness may be achieved.

During inflation of the balloon, support structure 4a combined with the outer wall and/or inner wall membrane (s)) will preferably have no or very limited increase in diameter under higher fluid pressures within its interior. The cup should be able to withstand pressure increases of up to 1000 mmHg with a limited increase in diameter, about 1-5% in diameter or less. To prevent possible outward expansion during inflation the membrane/outer wall 4b is preferably made of a limited compliant or non-compliant material. The membrane/outer wall 4b is built from or coated with a material that has limited to no interaction with blood. The material is selected to be flexible and durable, such as nylon or polyurethane with high durometer values. This can be achieved by using a polymer with high tensile modulus e.g. tecothane 72D. The membrane/outer wall 4b is attached or encapsulates the support structure 4a. The membrane/outer wall 4b itself has a wall thickness of e.g. between 10-100 μm for a single layer. The connection of the membrane/outer wall 4b to the support structure 4a is made such that the expandable cup 4 can be folded to a diameter of e.g. less than 6 mm, preferably about 3 mm, in the transport state, and expanded to a diameter of 10-25 mm, e.g. about 18 mm, in the operational state. The cup 4 may also include circumferential fibres of a material with a high tensile strength such as Kevlar, spectra, or other such materials attached, embedded within, or woven into the support structure 4a and/or outer wall 4b, which further limit the distensibility of the support structure 4a beyond its desired size, while still allowing it to be collapsed into the transport state for insertion and removal.

The cup preferably has a high elastic recoil, which creates higher shape consistency during both inflation and the deflation, with elastic deformation preferably being limited to about 0.1% and −3%, and +0.1-10% with a preferred range of −0.5 and +1%. The higher shape consistency during pumping has multiple positive effects: First, it improves the energy transportation, making the device more efficient in transporting the blood. Second, the higher stiffness allows the balloon to be operated at a higher inflation-deflation frequency. Third, this effect decreases the impact of pressure waves on the cardiovascular environment (i.e. tissues such as the heart and vasculature). Fourth, by having smaller pulses, device buoyancy (due to helium) is reduced, and the stability of the device is improved. Furthermore, a smaller balloon with higher frequency inflation may result in reduced reaction forces and less oscillation, allowing it to act more like a continuous pump.

As illustrated in FIGS. 9A-C, to facilitate endovascular delivery and removal, the assist device 1, in the transport state, is preferably positionable in the inner lumen of a sheath 36 (shown in FIG. 9A). Expandable cup 4 may be crimped with a crimping tool into the transport state, or in some embodiments, may collapse by being advanced into a proximal end of sheath 36 or drawn proximally into the distal end of sheath 36. A guidewire GW may extend slidably through a guidewire lumen in at least a distal portion of catheter assembly 3 within expandable cup 4, over which the heart assist device 1, contained within sheath 36 may be advanced through the vascular system to the desired location for operation. Once positioned in the desired location in the cardiovascular system, sheath 36 may be retracted relative to device 1 such that cup 4 expands into the operational state, shown in FIG. 9C. After usage the heart assist device 1 needs to be safely removed from the body. This may be done by collapsing cup 4 back to the transport state in the body. Device 1 may be retracted into sheath 36 such that sheath 36 compresses the cup 4 back into a transport state. To allow cup 4 to smoothly collapse as it is drawn into sheath 36, proximal (downstream) end 38 of the outflow nozzle 6 is preferably tapered, rounded or ellipsoid in shape, as shown in FIGS. 10A-B. The downstream tip 40 of the tapered end 38 may be connected to retrieval wire or shaft 42 which may extend through the delivery sheath from a point outside the patient, as shown in FIG. 10B. Alternatively, the downstream tip 40 may include an eyelet 44, or knob, loop, hook, or other means, to which a retrieval device, wire or snare 46 may be connected when the heart assist device is to be removed, as shown in FIG. 10C.

In further embodiments, the cardiac assist device is configured to operate with an inert fluid in the catheter assembly 3 and the inflatable balloon 8 for inflating and deflating the inflatable balloon 8. This assists in operating the heart assist device at a relatively high frequency. The inert fluid is e.g. a low viscosity fluid such as helium or carbon dioxide, to minimize friction with inside walls of the catheter assembly. Helium has the additional advantage of having a low density, therefore a lower mass inertia, allowing higher inflation frequencies. To achieve large volume displacement the inflatable balloon 8 is inflated and deflated with a low viscosity medium (e.g. helium) at a tunable or predetermined frequency. The inflatable balloon 8 is connected to the catheter assembly 3, which is optimized for high flow, as described below. The parts in contact with the inert fluid are the catheter assembly, a driver part of the control unit 2 and the inflatable balloon 8. The total volume of inert fluid is e.g. about 16 ml (with a range of e.g. between 2 ml and 35 ml), which is sufficiently low to enable high frequency operation.

The inflatable balloon 8 is, in a further embodiment, a directional operating balloon, arranged to allow inflow of fluid into the expandable cup 4 when deflating, and to allow (directed) outflow of the fluid through the outflow nozzle 6. The balloon may be configured to inflate first in its distal portion (furthest away from the outflow nozzle), and to sequentially inflate in a downstream direction such that a proximal portion (closest outflow nozzle) inflates last. Directional inflation can be achieved by shape (e.g.) a conically shaped balloon, various wall thickness (higher wall thickness in the area to inflate last) or various durometers of the balloon (higher durometer material in the area to inflate last). In exemplary embodiments, the inflatable balloon 8 can be made of varying wall thickness along a longitudinal axis of the heart assist device 1 to obtain a predetermined inflation pattern, e.g. starting at the distal end of the expandable cup 4, moving upwards in a direction toward the outflow nozzle 6.

The inflatable balloon 8 is designed to prevent any kind of outflow blockage from pumping chamber 30, e.g. by having a smaller diameter than the internal diameter of the expandable cup 4 at the area of the outflow nozzle 6. As shown in FIG. 11A-D, the pumping chamber 30 may have an outflow opening 50 through which blood flows out of the pumping chamber 30, and the shape and size of the cup 4 and balloon 8 are selected so as to maintain a space between the inflated balloon 8 and the outflow opening 50 and to minimize resistance to the flow of blood out of the chamber (shown by arrows B). In some embodiments, the inflatable balloon may be attached to the expandable cup at a distal end 51 of the expandable cup remote from the outflow opening 50, which helps to anchor the balloon in a fixed position relative to the cup, minimizing movement of the balloon relative to the cup (other than from inflation) and reducing vibration. The inflatable balloon 8 e.g. has a volume of about 8 ml when inflated (preferably within a range of 0.3-20 ml). The material of the inflatable balloon 8 is e.g. a durable, thin ideally 20 um (10-60 μm), single wall material, such as polyurethane or nylon. In an exemplary embodiment, balloon 8 is made of Pellethane 55D, of a material with similar mechanical properties, and has a single wall thickness of 10-60 microns, ideally about 20 microns.

In specific embodiments, heart assist device 1 is configured to provide the desired blood flow rates for the particular procedure and patient condition, while limiting hemolysis below acceptable thresholds. Hemolysis can be caused by the imposition of excessive shear stresses on red blood cells for excessively long time periods. Heart assist device 1 of the invention is configured to limit the magnitude of shear stresses to which red blood cells are subject and to minimize the time red blood cells are subject to such shear stresses as they pass through heart assist device 1. For support during high-risk PCI procedures, heart assist device 1 may produce flows of at least 3 L/min, while limiting shear stresses to no more than 100 Pa. For treating cardiogenic shock, heart assist device 1 may produce flows of at least 5 L/min, while limiting shear stresses to no more than 400 Pa. In particularly high-flow embodiments, heart assist device 1 may produce flows of at least 6 L/min while limiting shear stresses to no more than 3000 Pa.

Preferably the expandable cup 4 and inflatable balloon 8 are configured to maximize flow and minimize hemolysis. As shown in FIG. 11A-D, when the balloon 8 is in its inflated configuration and the cup 4 in the operational state, a spacing 52 of at least about 0.05-1.5 mm is preferably maintained between the balloon 8 and an interior wall of the cup 4 which helps to limit hemolysis during high frequency balloon inflation. The balloon 8 is configured such that its maximum inflated diameter is less than the inner diameter of the cup, e.g. about 0.1-3 mm less in diameter, when the pressure inside balloon 8 is at least about 600 mmHg. This size difference avoids cavitation which may occur when the balloon 8 is in direct contact with the inner wall or membrane of the cup 4. Furthermore, the spacing between the balloon 8 and the cup 4 avoids potentially locking blood in the pumping chamber 30 (compartmentation). Lastly, the room between the balloon 8 and the cup 4 minimizes the shear stress on the erythrocytes during the last part of the ejection phase, when the balloon 8 is close to the cup wall, thereby reducing hemolysis. A spacing 52 of about 0.1 mm is sufficient to keep the shear stresses sufficiently low (less than 100 Pa at 3 L/min, or less than 400 Pa at 5 L/min). Also, the exposure time to this shear rate is low (less than 5 ms) is such that the threshold for hemolysis is not reached.

The catheter assembly 3 of the various present invention embodiments is also provided with specific features allowing or enhancing the high frequency operation of the heart assist device, and/or to optimize inert fluid (helium) flow. In a first exemplary embodiment, shown in FIGS. 12A-F, in which catheter assembly 3 is shown extending through a delivery sheath 36, the catheter assembly 3 comprises a balloon shaft 54, having an inflation lumen 56 with a cross sectional flow area of between 1 and 20 mm2. This corresponds to an inner diameter of generally between 0.5 and 5 mm, which allows a proper balance between flow resistance for the inert fluid and further characteristics of the catheter parts, such as bending radius, kinking resistance, etc. In preferred embodiments, the inflation lumen 56 will be not subdivided, since the resistance will go up when the cross-sectional area is distributed over different channels. The shape of the inflation lumen 56 should be configured to have the lowest resistance possible, while leaving room in the catheter assembly for a potential guidewire, pull wires for device retrieval and potential sensors.

In preferred embodiments, shown in FIGS. 12B-E, the balloon shaft 54 preferably comprises 3 or more lumens, including inflation lumen 56, which will usually be largest in diameter, a guidewire lumen 58, and one or multiple wire lumens 60 for pull wire(s) for retrieval. Catheter assembly 3 may further comprise one or more sensors at or near its distal end, e.g. pressure transducers for measuring pressures within the pumping chamber 30 of cup 4 or in the heart outside cup 4, heart rate sensors, or other sensors, and balloon shaft 54 may include lumens for wires to such sensors.

In a further embodiment, a distal section of the catheter assembly 3 has a wider diameter than a proximal section of the catheter assembly, the proximal section being farther from the inflatable balloon 8 than the distal section. The allows the inflation lumen in the distal section of the catheter assembly 3, to be larger than in the proximal section, and thereby lower friction to the inert inflation fluid in the larger distal section. The distal section may be configured to be positioned in the larger vessels further toward the heart from the point of introduction, such as in the aorta. As an example, the diameter in a distal section of the catheter assembly 1 may be 60 mm long with a diameter of 2.2 mm, and a proximal section (in the aorta, femoral area, and outside the patient) may be 1200 mm long and a diameter of 2.5 mm.

The catheter assembly 3 may further comprise a plurality of catheter sections with different diameter. The wider diameter sections are e.g. configured for use in areas where blood flow is not obstructed (e.g. peripheral arteries) or where they remain outside of a patient during operation. In an example, a first section (within expandable cup 4) is 60 mm long with a diameter of 2.2 mm, a second section (in the aorta area) is 800 mm long with a diameter of 3 mm, a third section (in the femoral area) is 400 mm long and a diameter of 2.5 mm, and a fourth section (outside the patient) has a length of 750 mm and a diameter of 4 mm.

In an even further embodiment, the catheter assembly 3 comprises a stiff material selected 10 to provide a low flow resistance (i.e. a low impedance to the inflation and deflation pressures during operation) as well as kink resistance. In further embodiments, the catheter assembly 3 comprises nylon material with a wall thickness of between 0.1 and 0.3 mm, e.g. 0.2 mm. Dedicated catheter material and dimension choices allow preservation of the radial shape, while being sufficiently flexible in the longitudinal direction. The shaft will have a high radial stiffness, achieved by high durometer material, e.g nylon 12 pebax or polyimide of 72D or higher wall thickness, reinforced with a braid or coil of wire or ribbon. The high durometer helps for rapid transport of helium. The durometer may vary over the shaft length to accommodate the curvature of the vasculature or ascending aorta.

The catheter assembly 3 in a further embodiment comprises a thermally isolating coating layer, e.g. Al, over its exterior. This will help to maintain the (relative) low temperature of the inert fluid, such as helium, thereby giving it higher density and allowing higher flow velocities. Additionally or alternatively, the control system 2 may be provided with an active cooling subsystem for controlling the temperature of the inert fluid delivered to the catheter assembly 3 during operation. In exemplary embodiments, the inflation fluid may be cooled and maintained at a temperature between –20 c and 20 c.

Catheter assembly 3, along with expandable cup 4, are configured to minimize vibration or oscillation when operated at high frequency. When blood is ejected from the pumping chamber 30 of cup 4 by inflation of the balloon 8, the resulting thrust leads to a force into the opposite direction. The thrust caused by the blood leaving the pumping chamber through the outflow nozzle 6 into the aorta leads to a counter-force which can move the expandable cup 4 from its equilibrium position to a position deeper into the left ventricle. Once the pump stroke has been completed, the expandable cup 4 will seek to return into its equilibrium position, driven by the pull from the catheter assembly 3 and the push from the distal tip of the device. The size, geometry, and stiffness of balloon shaft 54 may be selected such that it acts to dampen this motion of expandable cup 4. Further, by operating the volume displacement member, e.g. balloon 8, at a sufficiently high frequency, the next pump stroke will happen before the device has time to relax and return to its equilibrium position. In this case, the device will be "trapped" in a position away from its equilibrium position. The higher the frequency, the less time the device has to move back towards its equilibrium position, and the more stable the device tip will be.

Figure 4:
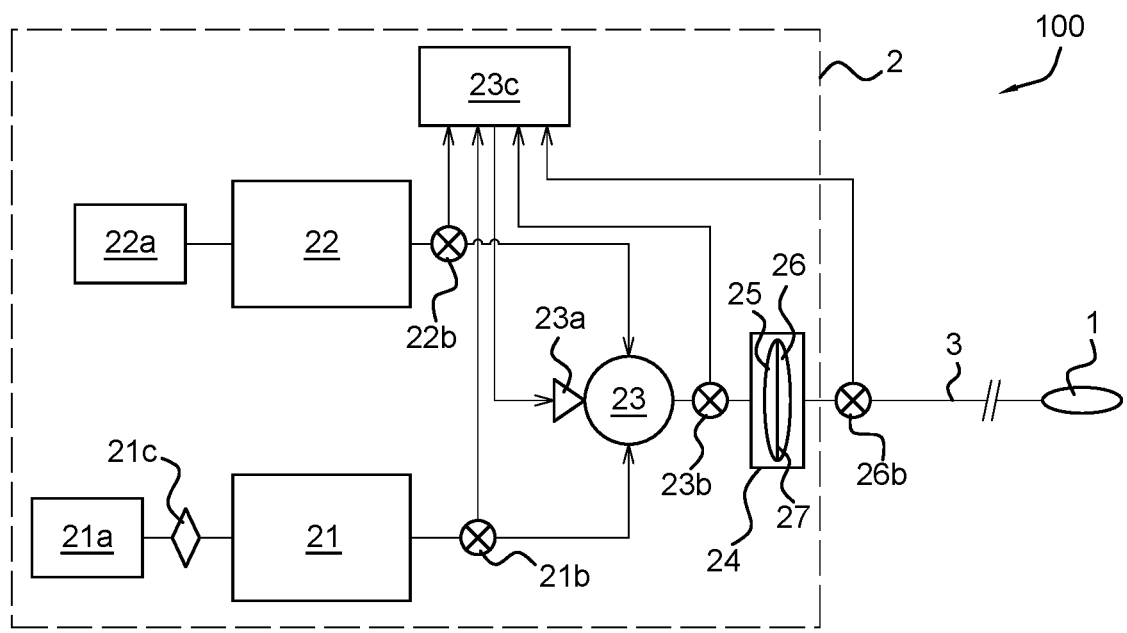
FIG. 4 shows a schematic diagram of a control unit of a heart assist device according to an embodiment of the present invention.
Figure 5A:
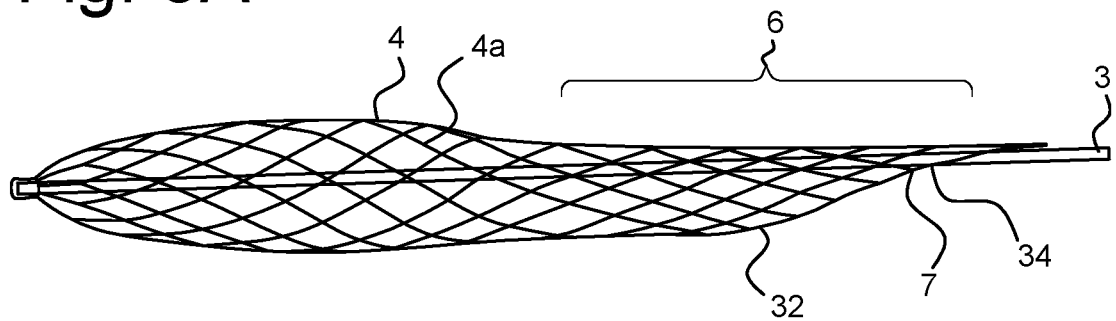
FIGS. 5A and 6A are side elevational views of a distal portion of a heart assist device according to the invention, showing an outflow valve thereof in closed and open positions, respectively.
Figure 5B:
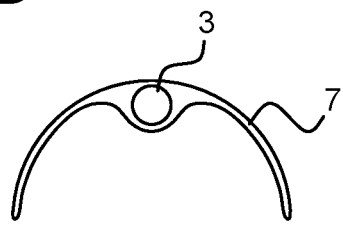
FIGS. 5B and 6B are transverse cross-sections of the heart assist device of FIGS. 5A and 6A, respectively.
Figure 6A:
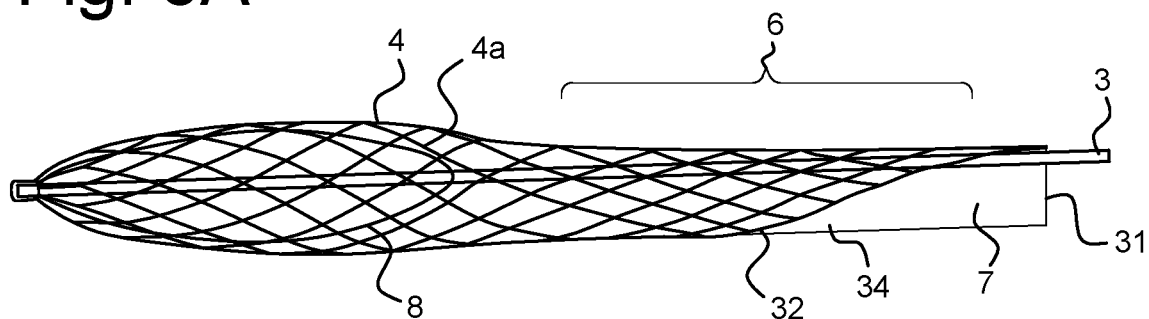
Figure 6B:
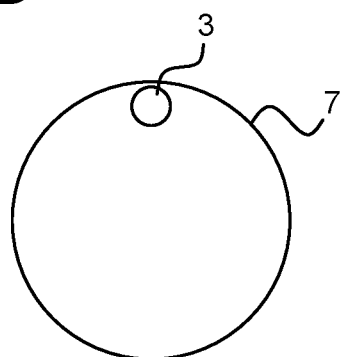
Figure 7A:
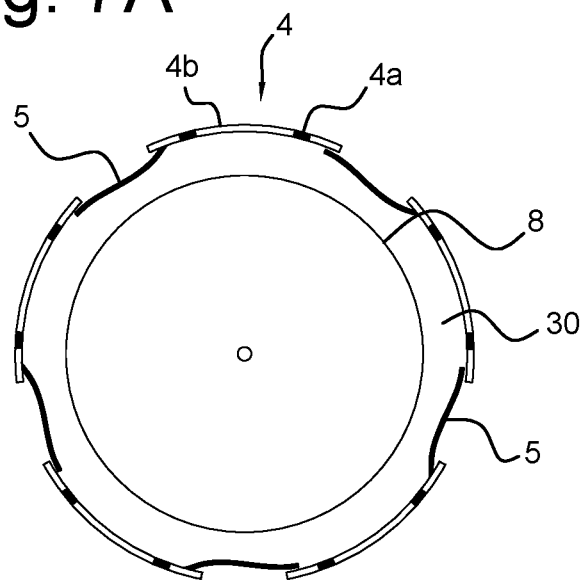
FIGS. 7A and 8A are transverse cross-sections of an expandable cup of a heart assist device according to the invention, with an inflatable balloon in inflated and deflated configurations, respectively.
Figure 7B:
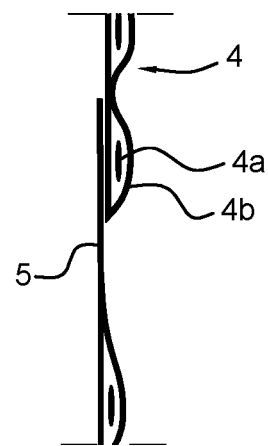
FIGS. 7B and 8B are cross-sectional views of a portion of a wall and inlet valve of the expandable cups shown in FIGS. 7A and 8A, respectively.
Figure 7C:
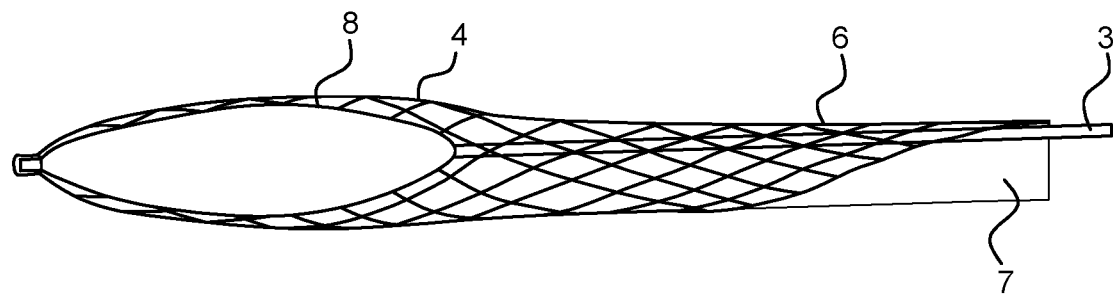
FIGS. 7C and 8C are side elevational views of the expandable cup of the heart assist device shown in FIGS. 7A-B and 8A-B, respectively.
Figure 7D:
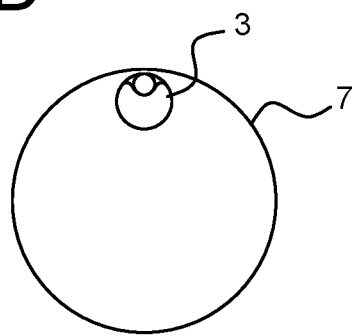
FIGS. 7D and 8D are transverse cross-sections of an outflow nozzle and outflow valve of 35 the heart assist device of FIGS. 7A-C and FIGS. 8A-C, respectively.
Figure 8A:
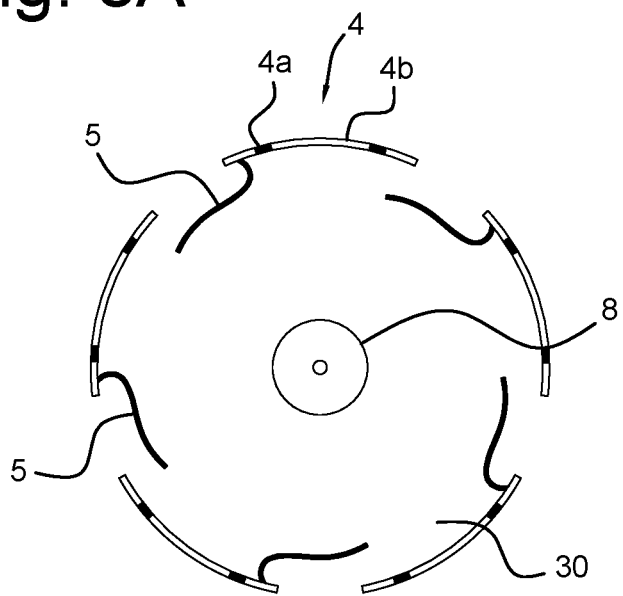
Figure 8B:
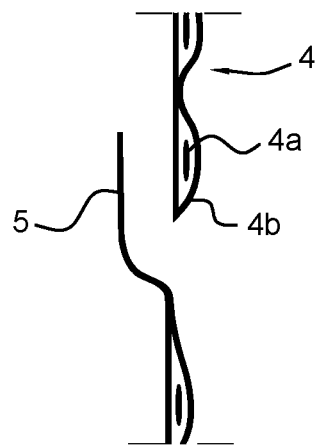
Figure 8C:
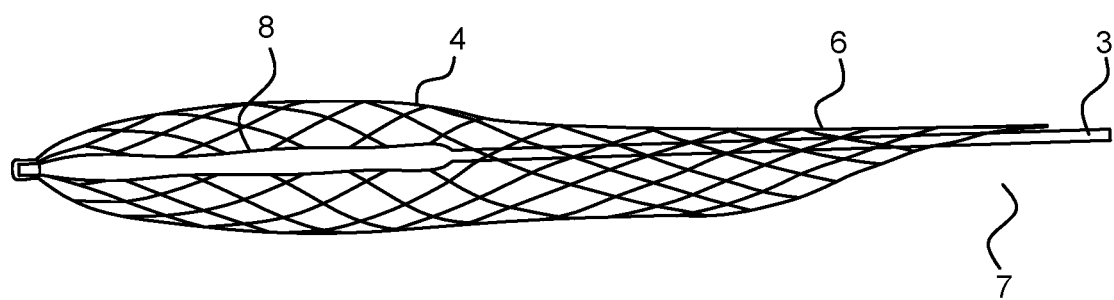
Figure 8D:
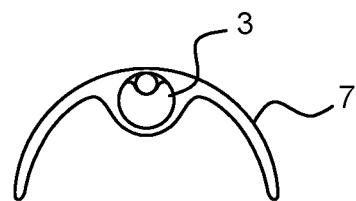

FIG. 4 shows a schematic diagram of details of an exemplary control unit 2 of a heart assist system 100 according to an embodiment of the present invention. In one embodiment, the control unit 2 comprises a high-pressure source 21, a low-pressure source 22, and a switching arrangement 23 connected to the high pressure source 21, the low pressure source 22 and the catheter assembly 3, the switching arrangement 23 being arranged to alternately connect the high-pressure source 21 and the low-pressure source 22 to the catheter assembly 3. This allows the control unit 2 to use commercially available hydraulic/pneumatic control components, with reliable and robust (bedside) operation. In the exemplary embodiment of FIG. 4, the high-pressure source 21 is implemented as a combination of a high-pressure buffer 21, high-pressure compressor 21a and regulator 21c (and optionally high-pressure sensor 21b). The low-pressure source 22 is implemented as a combination of a vacuum buffer 22, vacuum pump 22a and low-pressure sensor 22b. The switching arrangement 23 is implemented as a combination of a 3-way valve unit 23 controlled via switch valve 23a using e.g. a function generator 23c. The function generator 23c receives signals from the high-pressure sensor 21b, high pressure sensor 22b, and switch pressure sensor 23b, in order to properly drive the switch valve 23a. Connection to the catheter assembly 3 is implemented via a safety driver 24.

To allow high frequency operation of the 3-way valve unit 23, a valve design is selected to have an optimal flow through the valve, with minimal turbulence, high switch speed and low leak rate. The respective high- and low-pressure sources 21, 22 are e.g. connected with an angulation of less than 45 degrees, and a small difference in diameter between the tubing and the valve such that turbulent flow is minimized, and the flow towards the safety driver 24 is optimized.

The control unit 2 in an even further embodiment further comprises a safety driver 24 having a source side chamber 25 and a catheter side chamber 26 separated by a safety diaphragm 27. This allows the use of a pneumatic/hydraulic part of the control unit 2, separated from an inert gas side part of the control unit 2, to be connected to the catheter assembly 3, minimizing the volume of inert gas needed in the heart assist system 100. The safety driver 24 accommodates the actuation of the inert gas circuit, by compressing and expanding the inert gas circuit at the catheter side chamber 26 of the safety driver 24. The actuation speed of the safety driver is sufficient to e.g. provide a pressure difference between +800 to −800 mmHg, in a volume of e.g. 20 ml (typical range is 5-70 ml) within 5-200 ms.

In a group of embodiments, the control unit 2 is arranged to connect the high-pressure source 21 to the catheter assembly 3 during an inflation time period, and to connect to the low-pressure source 22 during a deflation time period, wherein the inflation time period is shorter than the deflation time period. In general inflation (high pressure) can be applied more quickly in a dynamic system than deflation (low pressure), providing for a more efficient operation for this embodiment. The inflation time period and deflation time period together form one operation cycle, and thus a duty cycle can be defined as the inflation time period percentage of a complete cycle, which is preferably less than 50%. In further exemplary embodiment, the duty cycle is less than 40% or even between 30 and 50%. In exemplary embodiments, a duty cycle of about 40% has proven to be most efficient for the heart assist device 1 of the present invention.

This duty cycle may be altered with variable counterpressure. With higher counterpressure, there may be a need for more inflation time, while the deflation may be faster, when the environmental pressure also reduces the balloon volume.

The control unit 2 furthermore may be arranged to respond to sensor data or user input. E.g. control unit 2 may be responsive to certain sensed counter pressures, or simply to create an additional pulsatile flow, by altering the speed of the inflation. Implementation can include, but is not limited to, responding to ECG triggered adaptations to switch between a lower frequency (e.g. 200 bpm) and a higher frequency (e.g. 700 bpm), operation of the heart assist device 1 for e.g. a period of 1 second each, or e.g. operation only during diastole or only during systole. Or a (brief) pause in inflation or deflation can be triggered at a specific moment in the cardiac cycle.

In the exemplary embodiment shown in FIG. 4, the driver 24 (or safety chamber) is sized relative to the total volume of the inert gas (helium) circuit. Safety diaphragm 27 may be movable so as to alter the volume of the inert gas circuit. By moving the safety diaphragm 27 into the source side chamber 25, the total volume of the inert gas circuit can be enlarged, thus depressurizing the inert gas circuit. Or by moving it in the opposite direction, the total volume of the inert gas circuit may be reduced, and thereby pressurized. With this actuation, helium pressures can be obtained in the inert gas circuit of e.g. between 600 mmHg and −600 mmHg in a 130 cm long catheter assembly 3 with a cross section area of e.g. 3 mm2 in order to inflate and deflate the inflatable balloon 8 within 10 ms.

To further optimize the translation of pressure from the safety diaphragm 27 to the inflatable balloon 8, the length of catheter assembly 3 should be minimized. Therefore, the safety diaphragm 27, and other components of the control unit 2 are adapted to be included in a bedside control unit 2, e.g. by using external versions of the high-pressure source 21 and low pressure source 22. The bedside control unit 2 can then be mounted to the bed a distance of 20-100 cm away, in some cases less than 30 cm away, from the vascular access site on the patient.

In the embodiment shown in FIG. 4, the inert gas circuit between safety diaphragm 27 and the inflatable balloon 8 is provided with an inert gas pressure sensor 26b, the signal of which can be provided to the function generator 23c for user information, driver control and/or failure detection functions. E.g. in the control unit 2, a continuous check for the pressure and wave forms is applied, to detect gas leak or kinking/obstruction of the catheter assembly 3. A diversion of the normal to be expected inert gas pressure signal provides information: When pressure drops it is a sign of inert gas leak, and the heart assist device 1 is stopped or switched to vacuum/low pressure control mode. Overpressure can be caused by kinking of the catheter assembly. More advanced software may be used in the control unit 2 to deduct the ventricular pressure from the inert gas (balloon) pressure.

ƒ In an even further embodiment, the safety driver 24 is cooled/heated to e.g. 10 degrees Celsius, in order to preserve the material properties, safety, and inert gas flow speed. As an alternative to this indirect temperature control of the inert fluid in the catheter assembly 3 during operation, the inert fluid temperature may be controlled using an active fluid cooling subsystem. Furthermore, the inert gas circuit may be further provided with an automatic filling system. E.g. to ensure stable helium concentration, every two hours (or periodically with an interval between 30 min and 4 hours) the helium system is emptied and there is an automatic injection of a new helium capsule. Such capsules can be replaced in the bedside safety driver 24 when needed.

In accordance with the methods of the invention, the heart assist devices and systems of the invention may be used to provide cardiac assist in a variety of procedures and to address a variety of patient conditions. For example, the cardiac assist devices and systems may be used for cardiac assist during high risk percutaneous coronary interventions (PCI) including angioplasty and stenting. Furthermore, the cardiac assist devices and systems may be used to provide cardiac support for patients experiencing cardiogenic shock. Furthermore, the cardiac assist devices and systems may be used to provide cardiac support for patients experiencing acute myocardial infarction. Generally, for such procedures, the heart assist devices will be configured for placement in the left ventricle, however placement at various other cardiovascular lumen sites is also possible, including in the ascending or descending aorta, the right atrium, right ventricle, or pulmonary artery.

In an exemplary embodiment of a method according to the invention, a heart assist device 1 is crimped into a transport state having a low-profile suitable for endovascular delivery. Usually, heart assist device 1 will be placed within the lumen of a tubular delivery sheath having an outer diameter less than about 18 Fr, more preferably less than 14 Fr, in some cases less than 10 Fr as described elsewhere herein. A guidewire may be inserted through the guidewire lumen of catheter assembly 3 and advanced into a peripheral artery such as the femoral artery (typically through an introducer sheath), preferably using percutaneous techniques. The guidewire may be advanced through the femoral and iliac arteries, aorta, and aortic valve into the left ventricle. The sheath, containing heart assist device 1, is then advanced over the guidewire into the femoral artery and through the vasculature and aortic valve into the left ventricle. The sheath may then be retracted relative to heart assist device 1, allowing expandable cup 4 to self-expand in the left ventricle to an operational state. The sheath is further retracted until outflow nozzle 6 has been deployed with its outflow end in the ascending aorta. Optionally, the sheath is withdrawn from the patient, or it may be left in place downstream of outflow nozzle 6.

A proximal end of catheter assembly 3 is coupled to control unit 2 outside the patient. Control unit 2 may then be activated to begin cyclical inflation and deflation of balloon 8 within cup 4. Preferably, control unit 2 includes a frequency controller allowing the user to vary the inflation frequency, speed and select a desired inflation frequency setting. In preferred embodiments, as described above, balloon 8 is cyclically inflated and deflated at a frequency of at least 2 times the patient's natural heartbeat, in some cases up to 10 times, and in other cases up to 100 times the natural heartbeat, which may be sensed using a cardiac monitor, heart rate sensor, ECG, or other means. In some embodiments, the means for sensing the natural heartbeat is electronically connected, either by wires or wirelessly, to the control unit 2, which is adapted to automatically vary the inflation frequency according to changes in heart rate. In other embodiments, inflation frequency may be set at a desired number of beats (inflation/deflation cycles) per minute, which may range from 200 to up to 10,000 cycles per minute, as described elsewhere herein. The inflation frequency may be set to be synchronous with the frequency of the natural heartbeat, to be a desired multiple or fraction of the natural heartbeat frequency, or to be completely independent of the natural heartbeat.

The blood flow rates produced by heart assist device may be varied by varying the inflation frequency of balloon 8. In high risk PCI procedures, flow rates of 3-4 L/min are typically needed. For patients in cardiogenic shock, higher flow rates are desirable, usually at least 5 L/min, preferably at least 6 L/min, and in some cases 8 L/min or more. Advantageously, the heart assist devices and systems of the invention can produce such high flow rates while having a low delivery profile for percutaneous delivery, a compact operational profile to minimize trauma to cardiac tissue, and a pumping mechanism which minimizes hemolysis.

Upon completion of the procedure or treatment, control unit 2 may be deactivated so that balloon inflation stops. The delivery sheath may be advanced distally relative to heart assist device 1 to a desired location, usually in the ascending aorta downstream of outflow nozzle 6. Heart assist device 1 may then be retracted by exerting traction on retrieval wires 62 until cup 4 is drawn into the internal lumen of the sheath. Advantageously, the tapered proximal end of outflow nozzle 6 facilitates capturing cup 4 in the sheath and collapsing cup 4 into a transport state as it is drawn into the sheath. The sheath containing heart assist device 1 may then by withdrawn from the patient and the femoral puncture or incision closed.

The present invention has been described above with reference to a number of exemplary embodiments as shown in the drawings. Modifications and alternative implementations of some parts or elements are possible, and are included in the scope of protection as defined in the appended claims.

We claim:

1. A cardiac assist system comprising:
    an expandable cup having a transport state and an operational state, the expandable cup comprising a pumping chamber and at least one inflow aperture;
    an outflow nozzle coupled to the expandable cup and in communication with the pumping chamber, wherein the outflow nozzle has a length and shape selected such that when the expandable cup is positioned within a left ventricle of a heart, an outlet of the outflow nozzle is downstream from an aortic valve of the heart;
    a volume displacement member positioned inside the expandable cup and movable between a low-volume state and a high-volume state;
    a catheter assembly connected to the volume displacement member during operation; and
    a control unit connected to the catheter assembly,
    wherein the control unit is configured to cyclically move the volume displacement member between the low-volume state and high-volume state at a frequency of at least 600 beats per minute (bpm).

2. The cardiac assist system of claim 1, wherein the control unit is configured to cyclically move the volume displacement member between the low-volume state and high-volume state at a frequency of between 600 bpm and 5,000 bpm.

3. The cardiac assist system of claim 1, wherein the volume displacement member comprises an inflatable balloon.

4. The cardiac assist system of claim 3, wherein the control unit is configured to deliver an inert fluid through the catheter assembly to the volume displacement member for inflating the balloon to achieve the high-volume state, and deflating the balloon to achieve the low-volume state.

5. The cardiac assist system of claim 4, wherein the control unit is configured to deliver the inert fluid through the catheter assembly at an inflation pressure of at least 200 mmHg.

6. The cardiac assist system of claim 3, wherein the system is configured to allow inflow of blood into the expandable cup through the at least one inflow aperture when the balloon is moving to the low-volume state, and to direct outflow of the blood through the outflow nozzle when the balloon is moving to the high-volume state.

7. The cardiac assist system of claim 3, wherein the balloon has a maximum inflated diameter that is less than an inner diameter of the expandable cup.

8. The cardiac assist system of claim 7, wherein the maximum inflated diameter is between 0.1 mm and 3 mm less than the inner diameter of the expandable cup.

9. The cardiac assist system of claim 1, wherein the expandable cup comprises a support structure.

10. The cardiac assist system of claim 9, wherein the support structure comprises one or more resilient metal wires.

11. The cardiac assist system of claim 9, wherein the expandable cup comprises a polymer membrane covering at least a portion of the support structure.

12. The cardiac assist system of claim 11, wherein the support structure is embedded in the polymer membrane.

13. The cardiac assist system of claim 9, wherein the support structure is configured to prevent collapse of the expandable cup under negative pressure within the pumping chamber down to −100 mmHg.

14. The cardiac assist system of claim 9, wherein the support structure of the expandable cup is a first support structure, and the outflow nozzle comprises a second support structure that is a monolithic extension of the first support structure.

15. The cardiac assist system of claim 14, wherein the outflow nozzle comprises a polymer membrane coupled to the second support structure.

16. The cardiac assist system of claim 15, wherein the polymer membrane covers at least a portion of the expandable cup and at least a portion of the outflow nozzle.

17. The cardiac assist system of claim 1, wherein the expandable cup in the operational state is substantially non-distensible under positive pressure within the pumping chamber of up to at least 400 mmHg.

18. The cardiac assist system of claim 1, wherein the expandable cup in the transport state has a delivery profile of no more than 18 Fr.

19. The cardiac assist system of claim 18, wherein the expandable cup in the transport state has a delivery profile of no more than 14 Fr.

20. The cardiac assist system of claim 1, wherein the control unit is configured to cyclically move the volume displacement member to produce a blood flow through the outflow nozzle of at least 5 L/min.

21. The cardiac assist system of claim 1, wherein the volume displacement member is configured to displace a volume of blood $V_d$ from the pumping chamber during each cycle, and wherein the control unit is configured to cyclically move the volume displacement member at a frequency F to produce a blood flow through the outflow nozzle at an exit flow rate R, where $R > F \cdot V_d$.

22. The cardiac assist system of claim 1, further comprising at least one one-way inflow valve associated with the at least one inflow aperture.

23. The cardiac assist system of claim 22, wherein the at least one inflow aperture is configured to convey inflow of blood through a wall of the expandable cup.

24. The cardiac assist system of claim 1, wherein the catheter assembly comprises an inflation lumen with a diameter of at least 1 mm.

25. The cardiac assist system of claim 1, wherein when the expandable cup is fully expanded, the outflow nozzle is not substantially smaller in diameter along its entire length than the pumping chamber.

26. A cardiac assist system comprising:
an expandable cup having a transport state and an operational state, the expandable cup comprising a pumping chamber and at least one inflow aperture, wherein the expandable cup comprises a first support structure and a polymer material covering at least a portion of an inner surface of the first support structure and at least a portion of the outer surface of the first support structure;
an outflow nozzle coupled to the expandable cup and in communication with the pumping chamber, wherein the outflow nozzle comprises a second support structure, wherein the outflow nozzle has a length and shape selected such that when the expandable cup is positioned within a ventricle of a heart, an outlet of the outflow nozzle is downstream from a cardiac valve adjacent to the ventricle;
a volume displacement member positioned inside the expandable cup and movable between a low-volume state and a high-volume state;
a catheter assembly connected to the volume displacement member during operation; and
a control unit connected to the catheter assembly,
wherein the control unit is configured to cyclically move the volume displacement member between the low-volume state and high-volume state at a frequency of at least 600 beats per minute (bpm).

27. The cardiac assist system of claim 26, wherein the second support structure is a monolithic extension of the first support structure.

* * * * *